(12) United States Patent
Okuno et al.

(10) Patent No.: US 10,849,582 B2
(45) Date of Patent: Dec. 1, 2020

(54) HOLDING MECHANISM FOR X-RAY IMAGING APPARATUS AND X-RAY IMAGING APPARATUS

(71) Applicant: Shimadzu Corporation, Kyoto (JP)

(72) Inventors: Tomoharu Okuno, Kyoto (JP); Shinji Hamasaki, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 58 days.

(21) Appl. No.: 16/328,544

(22) PCT Filed: Aug. 29, 2016

(86) PCT No.: PCT/JP2016/075142
§ 371 (c)(1),
(2) Date: Apr. 25, 2019

(87) PCT Pub. No.: WO2018/042483
PCT Pub. Date: Mar. 8, 2018

(65) Prior Publication Data
US 2019/0239835 A1   Aug. 8, 2019

(51) Int. Cl.
*A61B 6/00* (2006.01)
*A61B 6/10* (2006.01)

(52) U.S. Cl.
CPC ............. *A61B 6/4482* (2013.01); *A61B 6/00* (2013.01); *A61B 6/105* (2013.01); *A61B 6/4464* (2013.01)

(58) Field of Classification Search
CPC ......... A61B 6/4482; A61B 6/00; A61B 6/105; A61B 6/4464
See application file for complete search history.

(56) References Cited

U.S. PATENT DOCUMENTS

| | | | | |
|---|---|---|---|---|
| 3,866,048 A | * | 2/1975 | Gieschen | A61B 6/0457 378/91 |
| 3,986,090 A | * | 10/1976 | Hecker | A61B 6/4482 318/488 |
| 4,021,715 A | * | 5/1977 | Von Hacht | A61B 6/4482 318/628 |

(Continued)

FOREIGN PATENT DOCUMENTS

| | | |
|---|---|---|
| JP | H07-298681 A | 11/1995 |
| JP | 2000-116631 A | 4/2000 |

(Continued)

OTHER PUBLICATIONS

International Search Report dated Nov. 22, 2016 for PCT application PCT/JP2016/075142.

(Continued)

*Primary Examiner* — Blake C Riddick
(74) *Attorney, Agent, or Firm* — Muir Patent Law, PLLC

(57) ABSTRACT

This holding mechanism (3) for an X-ray imaging apparatus includes a switching means (36) that switches between a state of permitting movement of a moving body (4) including an X-ray tube (1) or an X-ray detector (2) and a state of prohibiting the movement, a force direction detection means (38) that detects a direction of a force applied to a moving mechanism (31), and a permission direction determination means (7) that determines a direction in which the movement is permitted by the switching means among a plurality of directions based on a detected direction of the force.

28 Claims, 8 Drawing Sheets

(56) References Cited

U.S. PATENT DOCUMENTS

| | | | | |
|---|---|---|---|---|
| 4,163,929 A * | 8/1979 | Janu | A61B 6/0457 | 318/628 |
| 4,208,586 A * | 6/1980 | Craig | A61B 6/4482 | 378/189 |
| 4,868,845 A * | 9/1989 | Koropp | A61B 6/4464 | 378/204 |
| 5,050,202 A * | 9/1991 | Yanome | A61B 6/4482 | 378/167 |
| 5,671,266 A * | 9/1997 | Linhart | A61B 6/4482 | 378/175 |
| 6,325,537 B1 | 12/2001 | Watanabe | | |
| 6,422,747 B2 | 7/2002 | Akutsu et al. | | |
| 7,177,393 B2 * | 2/2007 | Kanemitsu | A61B 6/105 | 378/114 |
| 2002/0084761 A1 | 7/2002 | Zettel et al. | | |
| 2004/0042587 A1 * | 3/2004 | Deshpande | A61B 6/4482 | 378/198 |
| 2005/0100134 A1 * | 5/2005 | Bauer | A61B 6/4482 | 378/197 |
| 2006/0120515 A1 * | 6/2006 | Ariyama | A61B 6/032 | 378/209 |
| 2006/0256921 A1 * | 11/2006 | Tachibana | G03B 42/026 | 378/116 |
| 2009/0257561 A1 * | 10/2009 | Okuno | A61B 6/545 | 378/116 |
| 2010/0215152 A1 * | 8/2010 | Takahashi | A61B 6/587 | 378/197 |
| 2012/0002790 A1 * | 1/2012 | Tanaka | A61B 6/0457 | 378/198 |
| 2012/0087479 A1 * | 4/2012 | Moon | A61B 6/547 | 378/189 |
| 2013/0121477 A1 * | 5/2013 | Lee | A61B 6/4476 | 378/198 |
| 2014/0093040 A1 * | 4/2014 | Omura | A61B 6/547 | 378/62 |
| 2014/0093046 A1 * | 4/2014 | Omura | A61B 6/547 | 378/98 |
| 2014/0105360 A1 * | 4/2014 | Yamanaka | G01N 23/04 | 378/62 |
| 2015/0090065 A1 * | 4/2015 | Kishi | A61B 34/37 | 74/491 |
| 2016/0270748 A1 * | 9/2016 | Garlow | A61B 6/4476 | |
| 2018/0085075 A1 * | 3/2018 | Zemanek | A61B 6/4482 | |

FOREIGN PATENT DOCUMENTS

| | | |
|---|---|---|
| JP | 2001-309910 A | 6/2001 |
| JP | 2001-258872 A | 9/2001 |
| JP | 2002-159479 A | 6/2002 |
| JP | 2003-010161 A | 1/2003 |
| JP | 2011-030699 A | 2/2011 |
| JP | 2015-150075 A | 8/2015 |
| WO | 2011/162149 A1 | 12/2011 |
| WO | 2012/043033 A1 | 4/2012 |

OTHER PUBLICATIONS

Written Opinion by the International Search Authority dated Nov. 22, 2016 for PCT application PCT/JP2016/075142, submitted with a partial translation (partial translation is a machine translation).

* cited by examiner (SECOND EMBODIMENT)

(THIRD EMBODIMENT)

(FOURTH EMBODIMENT)

(FIFTH EMBODIMENT)

(MODIFIED EXAMPLE)

HOLDING MECHANISM FOR X-RAY IMAGING APPARATUS AND X-RAY IMAGING APPARATUS

TECHNICAL FIELD

The present invention relates to a holding mechanism for an X-ray imaging apparatus and an X-ray imaging apparatus, and more particularly, it relates to a holding mechanism for an X-ray imaging apparatus, including a moving mechanism that movably holds an X-ray tube or an X-ray detector, and an X-ray imaging apparatus.

BACKGROUND ART

Conventionally, an X-ray imaging apparatus including a moving mechanism that movably holds an X-ray tube or an X-ray detector is known. Such an X-ray imaging apparatus is disclosed in International Publication No. 2012/043033, for example.

The X-ray imaging apparatus disclosed in International Publication No. 2012/043033 includes an X-ray tube device, a head (moving body) including an operation handle, a moving mechanism that movably holds the head, a locking mechanism that fixes movement of the head by the moving mechanism, and a controller that controls the locking mechanism. The moving mechanism movably holds the head in five axial directions, i.e. three orthogonal axial directions in horizontal and vertical directions, a rotational direction about an axis in the vertical direction, and a rotational direction about an axis in the horizontal direction. The locking mechanism can individually lock and unlock movement of the head in each of the five axial directions. The operation handle includes a plurality of unlocking switches corresponding to the respective axial directions, and when an operator operates the unlocking switch corresponding to any of the axial directions, the corresponding unlocking in the axial direction is performed by the controller.

When performing X-ray imaging of a person to be imaged (patient), the operator moves the head in an unlocked state to align the X-ray tube device, and performs imaging in a locked state.

PRIOR ART

Patent Document

Patent Document 1: International Publication No. 2012/043033

SUMMARY OF THE INVENTION

Problems to be Solved by the Invention

In the X-ray imaging apparatus disclosed in International Publication No. 2012/043033, when the moving body (head) is moved, it is necessary to operate the unlocking switch, and thus the operation is complicated. In particular, when the moving body is aligned, it is necessary for the operator to shift his or her gaze from an imaging position to the unlocking switch, and thus the usability (ease of use of a user or user-friendliness) is not satisfactory. When the moving body is rotated about the horizontal axis, for example, the position of the unlocking switch is also rotated about the horizontal axis before and after the rotation, and thus an intuitive operation cannot be performed. Therefore, it is desired to improve the operability when the moving body is moved.

The present invention has been proposed in order to solve the aforementioned problems, and an object of the present invention is to provide a holding mechanism for an X-ray imaging apparatus and an X-ray imaging apparatus, both of which can improve the operability when a moving body is moved for X-ray imaging.

Means for Solving the Problems

In order to attain the aforementioned object, a holding mechanism for an X-ray imaging apparatus according to a first aspect of the present invention includes a moving mechanism that holds a moving body including an X-ray tube or an X-ray detector such that the moving body is movable in a plurality of directions, a switching means that switches between a state of permitting movement of the moving body and a state of prohibiting the movement in each of the plurality of directions, a force direction detection means that detects a direction of a force applied to the moving mechanism, and a permission direction determination means that determines a direction in which the movement is permitted by the switching means among the plurality of directions based on a detected direction of the force. In the present description, the term "movement" indicates a broader concept including not only translating the moving body but also rotating the moving body. Moreover, the term "force applied to the moving mechanism" includes not only a force directly applied to the moving mechanism but also a force indirectly applied to the moving mechanism that holds the moving body by applying a force to the moving body.

As described above, the holding mechanism for an X-ray imaging apparatus according to the first aspect of the present invention includes the force direction detection means that detects the direction of the force applied to the moving mechanism and the permission direction determination means that determines the direction in which the movement is permitted by the switching means among the plurality of directions based on the detected direction of the force. Accordingly, when a force is applied to the moving mechanism (or the moving body), the permission direction determination means can switch the switching means to a state of permitting the movement in the direction in which the force is applied. Consequently, an operator can automatically switch the switching means to the state of permitting the movement in a direction (movement direction) in which the operator wishes to move the moving body and move the moving body simply by applying a force in the movement direction without a switch operation, for example. Thus, the operability at the time of moving the moving body for X-ray imaging can be improved. When the moving body is aligned, it is not necessary for the operator to shift his or her gaze from an imaging position, and thus the usability (ease of use of a user or user-friendliness) can be improved.

In the aforementioned holding mechanism for an X-ray imaging apparatus according to the first aspect, the plurality of directions preferably include horizontal and vertical translational directions orthogonal to each other, the moving mechanism preferably includes a support rod that holds the moving body such that the moving body is translatable in a vertical direction, and a grip supported by the support rod such that the grip moves integrally with the moving body, and the force direction detection means preferably detects a force in the vertical direction applied to the grip. According to this configuration, a portion to which the operator applies a force to permit the movement and a portion gripped by the operator to move the moving body can be matched. Consequently, the operator can permit the moving body to move in the vertical direction by performing an operation for moving the moving body in the vertical direction while holding the grip and can align the moving body while continuing the operation, and thus the operability can be further improved.

In this case, the moving mechanism preferably includes a traveling mechanism that supports the support rod such that the support rod is translatable in a horizontal direction, and the force direction detection means preferably detects forces in the horizontal and vertical translational directions applied to the grip. According to this configuration, even in the case of translation not only in the vertical direction but also in the horizontal direction, a portion to which the operator applies a force and a portion gripped by the operator can be matched. Consequently, the operability can be still further improved.

In the aforementioned configuration in which the moving mechanism includes the support rod, the traveling mechanism, and the grip, the force direction detection means preferably includes a force detector disposed between the grip and the support rod and capable of detecting forces in three orthogonal axial directions. According to this configuration, the shared force detector detects the forces in the horizontal and vertical translational directions, and the movement can be permitted. Therefore, the apparatus configuration can be simplified as compared with the configuration in which a force detector is individually provided for each of the three orthogonal axial directions.

In the aforementioned holding mechanism for an X-ray imaging apparatus according to the first aspect, the plurality of directions preferably include rotational directions about horizontal and vertical axes orthogonal to each other, the moving mechanism preferably includes a rotary holder that holds the moving body such that the moving body is rotatable about the horizontal axis, and a grip supported by the rotary holder such that the grip rotates integrally with the moving body, and the force direction detection means preferably detects a force in the rotational direction about the horizontal axis applied to the grip. According to this configuration, the operator can permit the movement of the moving body in the rotational direction about the horizontal axis by performing an operation for moving the moving body about the horizontal axis while holding the grip and can align the moving body while continuing the operation, and thus the operability can be further improved. Furthermore, unlike the case in which the position (operation position) of a switch or the like changes before and after the rotation about the horizontal axis such that the operability changes, and it is necessary to reconfirm the operation position, the operator can rotate the moving body simply by applying a force in a direction in which the operator wishes to move the moving body, and thus an intuitive operation is possible regardless of the direction of the moving body. Also in this point, the operability is improved.

In this case, the moving mechanism preferably includes a support rod that supports the rotary holder such that the rotary holder is rotatable about the vertical axis, and the force direction detection means preferably detects forces in the rotational directions about the horizontal and vertical axes applied to the grip. According to this configuration, in any of the rotational directions, the operator can permit rotational movement of the moving body in the movement direction simply by applying a force while holding the grip and can rotate the moving body while continuing to apply the force. Consequently, the operability can be still further improved.

In the aforementioned configuration in which the moving mechanism includes the support rod, the rotary holder, and the grip, the force direction detection means preferably includes a force detector disposed between the grip and the rotary holder and capable of detecting moments about a plurality of orthogonal axes. According to this configuration, the shared force detector can detect the force in the rotational direction about each of the axes and permit the rotational movement. Therefore, the apparatus configuration can be simplified as compared with the configuration in which a force detector is individually provided for each of the rotation axes.

In the aforementioned holding mechanism for an X-ray imaging apparatus according to the first aspect, the plurality of directions preferably include horizontal and vertical translational directions orthogonal to each other, and rotational directions about horizontal and vertical axes orthogonal to each other, and the force direction detection means preferably includes a force detector capable of detecting forces in the translational directions of three orthogonal axes and moments about the axes. According to this configuration, even in the configuration in which the moving body is movable in multiple directions, the shared force detector can detect the force in each of the movement directions and permit the movement. Therefore, even in the configuration in which the moving body is movable in multiple directions, it is not necessary to individually provide a force detector for each of the movement directions, and thus the apparatus configuration can be extremely simplified.

The aforementioned holding mechanism for an X-ray imaging apparatus according to the first aspect preferably further includes an operator detection means that detects an operator, and the permission direction determination means preferably controls the switching means to prohibit the movement when the operator is not detected by the operator detection means, and determines the direction in which the movement is permitted by the switching means when the operator is detected. According to this configuration, even in the configuration in which the movement of the moving body is automatically permitted based on the force applied to the moving mechanism, permission of the movement (the movement of the moving body) not intended by the operator can be prevented. Consequently, X-ray imaging can be performed at an intended position by preventing the unintended movement of the moving body while the usability in X-ray imaging is improved.

In this case, the moving mechanism preferably includes a grip that moves integrally with the moving body, and the operator detection means preferably detects that the grip is gripped by the operator. According to this configuration, using the fact that the operator grips the grip when moving the moving body, the operator can be easily and reliably detected.

In the aforementioned configuration including the operator detection means, the operator detection means preferably includes a communicator capable of wireless communication with a communication means held by the operator, and detects the operator via the communicator. According to this configuration, when the operator approaches while carrying the communication means in order to move the moving body, the operator can be easily detected. Furthermore, when the authentication information is included in the communication between the communication means and the communicator, personal authentication of the operator becomes possible, and an operation performed by an unauthorized third party can be prevented.

In the aforementioned holding mechanism for an X-ray imaging apparatus according to the first aspect preferably further includes a force strength detection means that detects a magnitude of the force applied to the moving mechanism, and an assisting means that applies an assisting force in a movement direction of the moving body to the moving body based on a detected magnitude of the force. According to this configuration, the force applied to the moving mechanism by the operator is detected such that not only permission of movement of the moving body but also power assistance for movement can be performed. Consequently, the operability can be significantly improved.

In this case, the plurality of directions preferably include horizontal and vertical translational directions orthogonal to each other, the moving mechanism preferably includes a support rod that holds the moving body such that the moving body is translatable in a vertical direction, and a grip supported by the support rod such that the grip moves integrally with the moving body, and the force strength detection means preferably detects a force in the vertical direction applied to the grip. According to this configuration, the operator simply moves the moving body in the vertical direction while holding the grip such that power assistance in the vertical direction can be performed by the assisting means, and thus the operability can be further improved.

In the aforementioned configuration in which the force strength detection means detects the force in the vertical direction applied to the grip, the moving mechanism preferably includes a traveling mechanism that supports the support rod such that the support rod is translatable in a horizontal direction, and the force strength detection means preferably detects forces in the horizontal and vertical translational directions applied to the grip. According to this configuration, the operator simply applies a force while holding the grip such that power assistance at the time of movement in an arbitrary translational direction can be performed by the assisting means, and thus the operability can be still further improved.

In the aforementioned configuration including the force strength detection means and the assisting means, the plurality of directions preferably include rotational directions about horizontal and vertical axes orthogonal to each other, the moving mechanism preferably includes a rotary holder that holds the moving body such that the moving body is rotatable about the horizontal axis, and a grip supported by the rotary holder such that the grip moves integrally with the moving body, and the force strength detection means preferably detects a force in the rotational direction about the horizontal axis applied to the grip. According to this configuration, the operator simply rotates the moving body about the horizontal axis while holding the grip such that power assistance in the rotational direction about the horizontal axis can be performed, and thus the operability can be further improved.

In this case, the moving mechanism preferably includes a support rod that supports the rotary holder such that the rotary holder is rotatable about the vertical axis, and the force strength detection means preferably detects forces in the rotational directions about the horizontal and vertical axes applied to the grip. According to this configuration, the operator simply applies a force while holding the grip such that power assistance at the time of movement in an arbitrary rotational direction can be performed. Therefore, power assistance by the assisting means can be started by the common operation of simply applying a force in the movement direction, and thus the operability can be still further improved.

The aforementioned configuration including the force strength detection means and the assisting means preferably further includes a force detector that detects the direction of the force and the magnitude of the force, and the force detector preferably includes the force direction detection means and the force strength detection means that are integral and unitary with each other. According to this configuration, the same force detector can include the force direction detection means and the force strength detection means, and thus the apparatus configuration can be simplified as compared with the configuration in which the direction of the force and the magnitude of the force are detected by separate detectors.

In the aforementioned configuration including the force strength detection means and the assisting means, the assisting means preferably applies, to the moving body, the assisting force having a magnitude corresponding to the detected magnitude of the force. According to this configuration, an assisting force is increased as a force applied by the operator is increased such that the moving body can be easily (lightly) moved. Therefore, even a heavy moving body can be quickly moved, and thus the usability in X-ray imaging can be further improved.

In the aforementioned holding mechanism for an X-ray imaging apparatus according to the first aspect, the moving mechanism preferably includes an engagement means that releasably engages with the moving mechanism to stop the moving body at a predetermined position, the switching means preferably switches to a state of prohibiting the movement of the moving body when the moving mechanism engages with the engagement means, and the permission direction determination means preferably determines the direction in which the movement is permitted by the switching means, and disengages the moving mechanism from the engagement means. According to this configuration, for example, the engagement means is provided with the position of the moving body at the time of standard X-ray imaging as the predetermined position such that the moving body can be easily and quickly positioned. Furthermore, even when the engagement means is provided, the operator simply applies a force to the moving mechanism such that the engagement means can be disengaged, and thus the operability can be improved.

In this case, the aforementioned holding mechanism for an X-ray imaging apparatus preferably further includes a force strength detection means that detects a magnitude of the force applied to the moving mechanism, and an assisting means that applies an assisting force in a movement direction of the moving body to the moving body based on a detected magnitude of the force, and the assisting means preferably decreases the assisting force to be applied to the moving body as the moving body is closer to the predetermined position when the moving body moves toward the predetermined position. According to this configuration, the force applied to the moving mechanism by the operator is detected such that power assistance for moving the moving body can be performed. Even when power assistance is performed, the moving body is made less likely to move (the assisting force is decreased) as the moving body is closer to the predetermined position such that the moving speed can be reduced, and thus the shock at the time of engaging the engagement means and the moving mechanism at the predetermined position can be mitigated.

The aforementioned holding mechanism for an X-ray imaging apparatus according to the first aspect preferably further includes a free mode setting means that controls the switching means to permit the movement of the moving body in all of the plurality of directions based on a setting operation of an operator. According to this configuration, after the setting operation of the operator is obtained, the moving body can be shifted to a free mode in which the moving body is freely movable. For example, after the moving body is roughly aligned in the free mode, only position adjustment in a specific movement direction can be performed by movement permission based on the detected direction of the force, and the usability (ease of use of a user or user-friendliness) can be still further improved.

In this case, the free mode setting means preferably switches the switching means to a state of prohibiting the movement in all of the plurality of directions based on a setting cancellation operation of the operator or a passage of time after permission of the movement in all of the plurality of directions. According to this configuration, it is easy to properly and selectively use movement permission in the free mode and movement permission based on the detected direction of the force.

In the aforementioned holding mechanism for an X-ray imaging apparatus according to the first aspect, the permission direction determination means preferably acquires imaging method information selected from two or three options among imaging in an upright position, imaging in a recumbent position, and general imaging, and switches, according to the imaging method information, between automatic determination control of determining the direction in which the movement is permitted based on the detected direction of the force and manual determination control of determining the direction in which the movement is permitted based on an operation input by an operator. According to this configuration, depending on the type of imaging method, control switching can be made such that the automatic determination control is performed for a predetermined imaging method that requires the movement of the moving body in an arbitrary direction, and the manual determination control is performed for another imaging method, for example. Consequently, control of determining the direction in which movement of the moving body is permitted can be properly and selectively used according to the purpose of the operator, and thus the usability can be further improved.

In this case, the permission direction determination means preferably acquires a reference position of the moving body based on the imaging method information, and in the automatic determination control, preferably permits the movement of the moving body in a movement direction in which a current position of the moving body is different from the reference position among the plurality of directions, based on the detected direction of the force, and prohibits the movement of the moving body in the movement direction in which the current position of the moving body coincides with the reference position. According to this configuration, even when the automatic determination control is performed, the moving body can be easily moved to the reference position set according to the imaging method.

In the aforementioned holding mechanism for an X-ray imaging apparatus according to the first aspect, the permission direction determination means preferably acquires imaging site information indicating a site to be imaged in X-ray imaging, and switches, according to the imaging site information, between automatic determination control of determining the direction in which the movement is permitted based on the detected direction of the force and manual determination control of determining the direction in which the movement is permitted based on an operation input by an operator. According to this configuration, depending on the imaging site, control switching can be made such that the automatic determination control is performed for a predetermined imaging site that requires the movement of the moving body in an arbitrary direction, and the manual determination control is performed for an imaging site that does not require the movement in the arbitrary direction, for example. Consequently, control of determining the direction in which the movement of the moving body is permitted can be properly and selectively used according to the purpose of the operator, and thus the usability (ease of use of a user or user-friendliness) can be further improved.

In this case, the permission direction determination means preferably acquires a reference position of the moving body based on the imaging site information, and in the automatic determination control, preferably permits the movement of the moving body in a movement direction in which a current position of the moving body is different from the reference position among the plurality of directions, based on the detected direction of the force, and prohibits the movement of the moving body in the movement direction in which the current position of the moving body coincides with the reference position. According to this configuration, even when the automatic determination control is performed, the moving body can be easily moved to the reference position set according to the imaging site.

In the aforementioned holding mechanism for an X-ray imaging apparatus according to the first aspect, the switching means is preferably constantly maintained in the state of prohibiting the movement of the moving body in each of the plurality of directions, and is preferably switched to a state of individually permitting the movement of the moving body in the direction determined by the permission direction determination means. According to this configuration, even when the movement of the moving body in the direction of the force applied by the operator is permitted, the movement of the moving body in the direction not intended by the operator can be significantly reduced or prevented.

In this case, the switching means preferably includes a plurality of locking mechanisms respectively corresponding to the plurality of directions and that lock the movement of the moving body, and unlocks one of the locking mechanisms corresponding to the direction determined by the permission direction determination means. According to this configuration, the movement only in the direction determined by the permission direction determination means can be easily and individually permitted, and the movement in the other directions can be continuously prohibited.

An X-ray imaging apparatus according to a second aspect of the present invention includes a moving body including an X-ray tube, an X-ray detector, a moving mechanism that holds the moving body such that the moving body is movable in a plurality of directions, a locking mechanism that releasably locks movement of the moving body in each of the plurality of directions, a force detector that detects a direction of a force applied to the moving mechanism, and a controller that controls the locking mechanism to unlock the movement in the direction of the force detected by the force detector among the plurality of directions. Note that the term "force applied to the moving mechanism" includes not only a force directly applied to the moving mechanism but also a force indirectly applied to the moving mechanism that holds the moving body by applying a force to the moving body.

As described above, the X-ray imaging apparatus according to the second aspect of the present invention includes the force detector that detects the direction of the force applied to the moving mechanism, and the controller that controls the locking mechanism to unlock the movement in the direction of the force detected by the force detector among the plurality of directions. Accordingly, when a force is applied to the moving mechanism (or the moving body), the controller can unlock the movement in the direction in which the force is applied, and permit the movement of the moving body. Consequently, an operator can automatically unlock the movement in a direction (movement direction) in which the operator wishes to move the moving body and move the moving body simply by applying a force in the movement direction without a switch operation, for example. Thus, the operability at the time of moving the moving body for X-ray imaging can be improved. When the moving body is aligned, it is not necessary for the operator to shift his or her gaze from an imaging position, and thus the usability (ease of use of a user or user-friendliness) can be improved.

Effect of the Invention

As described above, according to the present invention, it is possible to improve the operability when the moving body is moved for X-ray imaging.

MODES FOR CARRYING OUT THE INVENTION

Embodiments embodying the present invention are hereinafter described on the basis of the drawings.

First Embodiment (Configuration of X-Ray Imaging Apparatus)

The overall configuration of an X-ray imaging apparatus 100 according to a first embodiment of the present invention is now described with reference to FIGS. 1 to 7.

Figure 1:
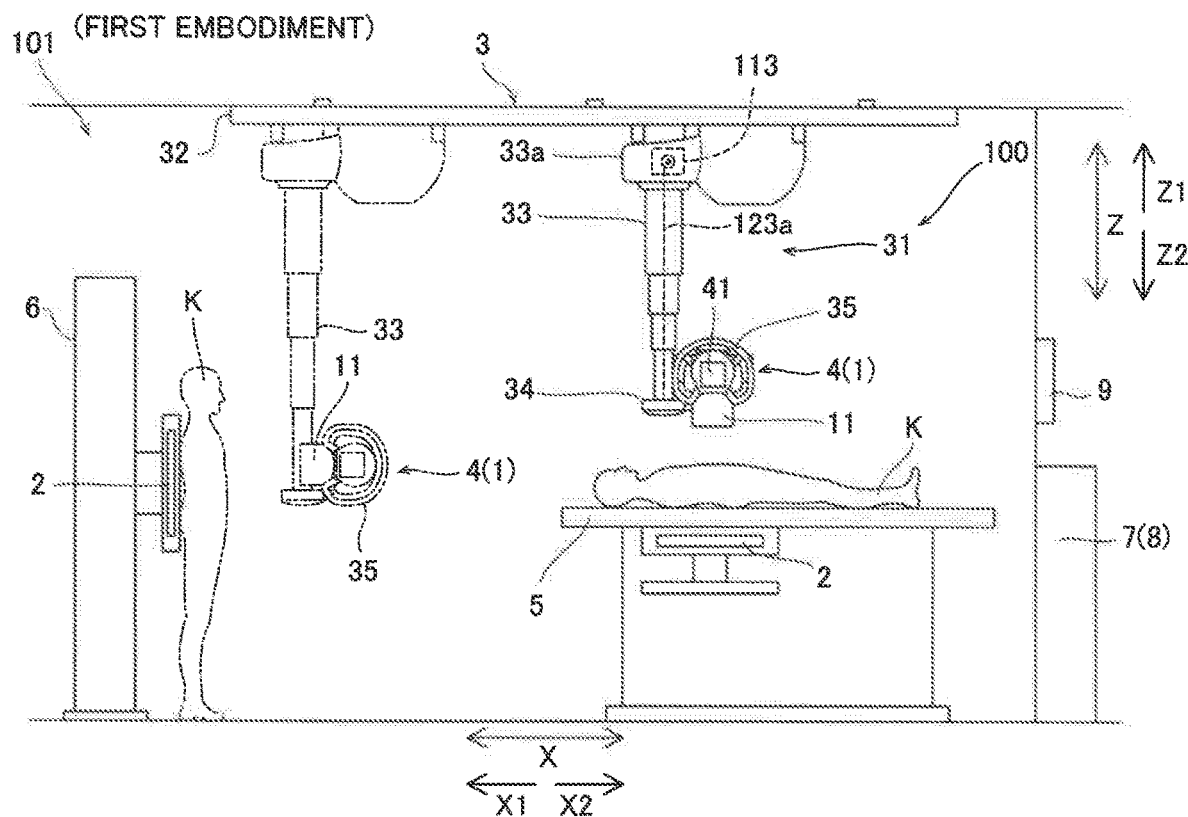
FIG. 1 is a schematic view showing the overall configuration of an X-ray imaging apparatus according to first to fifth embodiments.

FIG. 1 shows an example of a ceiling-suspended X-ray imaging apparatus 100 installed in an imaging room 101. The X-ray imaging apparatus 100 mainly includes an X-ray tube 1, an X-ray detector 2, and a holding mechanism 3. In the ceiling-suspended X-ray imaging apparatus 100, the holding mechanism 3 disposed on the ceiling of the imaging room 101 holds a moving body 4 including the X-ray tube 1 such that the moving body 4 suspends from the ceiling. The moving body 4 is movably held in the imaging room 101 by the holding mechanism 3. The holding mechanism 3 is an example of a "holding mechanism for an X-ray imaging apparatus" in the claims.

The X-ray imaging apparatus 100 is a medical X-ray imaging apparatus, and performs X-ray imaging of a patient K to be imaged. The X-ray imaging apparatus 100 includes an imaging table 5 to perform imaging in a posture in which the patient K lies down (in the recumbent position) and an imaging stand to perform imaging in a posture in which the patient K is upright (in the upright position).

The X-ray detector 2 is movably held by each of the imaging table 5 and the imaging stand 6. The X-ray detector 2 is a flat panel detector (FPD), for example. The holding mechanism 3 can move the moving body 4 at least between an imaging position (see solid lines in FIG. 1) in the recumbent position using the imaging table 5 and an imaging position (see two-dot chain lines in FIG. 1) in the upright position using the imaging stand 6.

In imaging in the recumbent position, the moving body 4 is disposed at a position that faces the X-ray detector 2 of the imaging table 5 in an upward-downward direction, and the patient K lying on the imaging table 5 is imaged between the X-ray tube 1 and the X-ray detector 2 that face each other in the upward-downward direction. In imaging in the upright position, the moving body 4 is disposed at a position that faces the X-ray detector 2 of the imaging stand 6 in a horizontal direction, and the patient K standing in front of the imaging stand 6 is imaged between the X-ray tube 1 and the X-ray detector 2 that faces each other in the horizontal direction. The portable X-ray detector 2 is disposed at an arbitrary position in the imaging room 101, and the moving body 4 is moved to a position that faces the X-ray detector 2 such that the X-ray imaging apparatus 100 can perform general imaging (imaging in which the posture is not specified) in which the patient K in an arbitrary posture can be imaged from an arbitrary direction.

Figure 2:
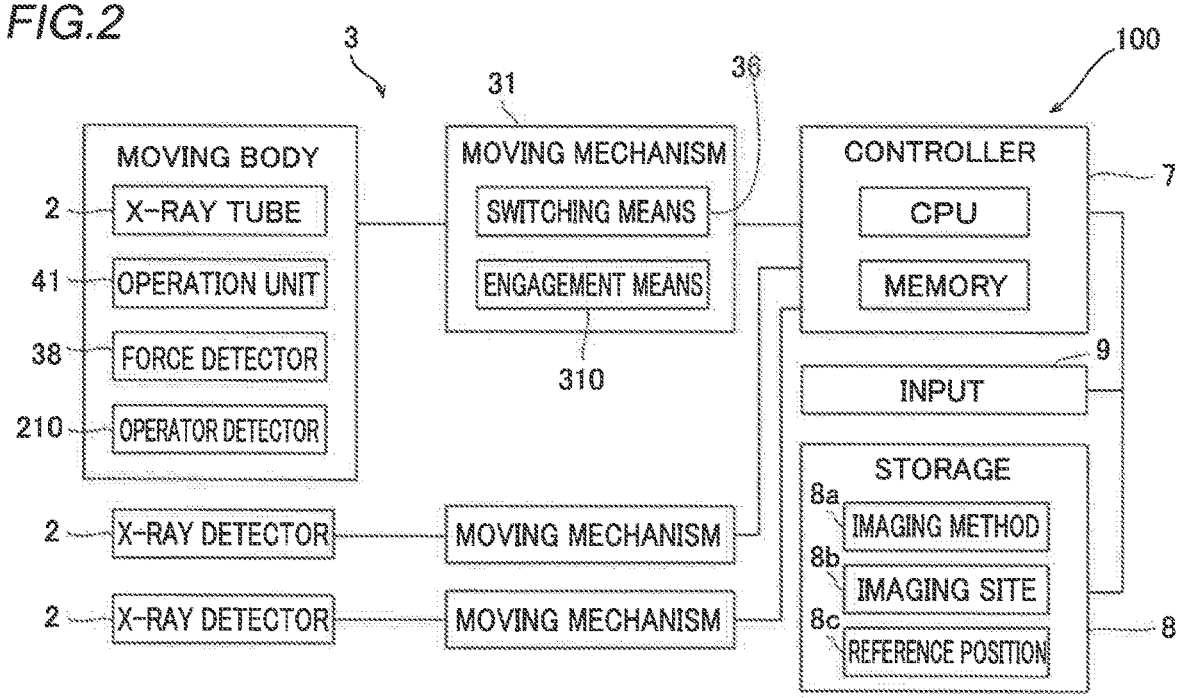
FIG. 2 is a block diagram of the X-ray imaging apparatus.

The X-ray imaging apparatus 100 also includes a controller 7, a storage 8, and an input 9. As shown in FIG. 2, the controller 7 mainly includes a CPU (Central Processing Unit) and a memory. The controller 7 controls X-ray imaging with the X-ray tube 1 and the X-ray detector 2 and controls movement of the moving body 4. The storage 8 stores various data used for X-ray imaging. The input 9 has a function of receiving an input operation related to X-ray imaging. The input operation includes setting of imaging conditions for X-ray imaging, an instruction to start X-ray irradiation, etc.

<Moving Body>

Returning to FIG. 1, the moving body 4 includes the X-ray tube 1 and a collimator 11. A high voltage is applied from a power supply (not shown) to the X-ray tube 1 such that the X-ray tube 1 generates X-rays. The collimator 11 includes a plurality of shielding plates (collimator leaves), the positions of which can be adjusted, and has a function of adjusting an X-ray field by shielding a portion of X-rays from the X-ray tube 1. In addition, the moving body 4 includes a grip 35. Furthermore, the moving body 4 includes an operation unit 41 including a touch panel or a mechanical switch.

<Holding Mechanism>

The holding mechanism 3 includes a moving mechanism 31 that holds the moving body 4 such that the moving body 4 is movable in a plurality of directions, and a switching means 36 (see FIG. 2) that switches between a state of permitting movement of the moving body 4 in each of the plurality of directions and a state of prohibiting movement of the moving body 4 in each of the plurality of directions.

The plurality of directions in which the moving mechanism 31 can move the moving body 4 can include horizontal and vertical translational directions orthogonal to each other. Assuming that a vertical (perpendicular) direction is a Z direction and two directions orthogonal to each other in the horizontal direction are an X direction and a Y direction (see FIG. 3), as shown in FIG. 1, the translational directions indicate one or a plurality of these X, Y, and Z directions.

The plurality of directions in which the moving mechanism 31 can move the moving body 4 can include rotational directions about horizontal axes and a vertical axis orthogonal to each other. The rotational directions indicate one or a plurality of the rotational direction about the vertical (perpendicular) axis and the rotational directions about two axes orthogonal to each other in the horizontal direction. In the first embodiment, an example in which the plurality of directions are five directions in total including three translational directions (X, Y, and Z directions), a rotational direction about a Z-axis (η direction; see FIG. 4), and a rotational direction about an R-axis in the horizontal direction (θ direction; see FIG. 4) is shown.

The moving mechanism 31 includes a traveling mechanism 32, a support rod 33, and a rotary holder 34, as shown in FIG. 1. The traveling mechanism 32 is provided on the ceiling of the imaging room 101. The traveling mechanism 32 supports the support rod 33 such that the support rod 33 (moving body 4) can translate in the X direction and the Y direction.

Figure 3:
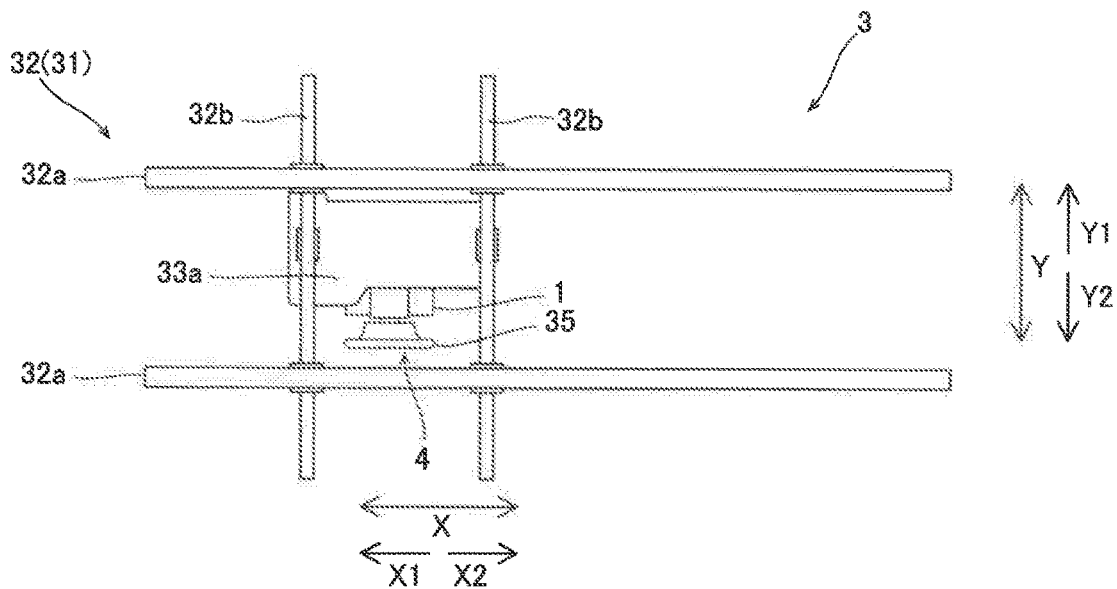
FIG. 3 is a plan view schematically showing a traveling mechanism.

Specifically, as shown in FIG. 3, the traveling mechanism 32 includes a pair of fixed rails 32a fixed to the ceiling surface and a pair of movable rails 32b. The pair of fixed rails 32a linearly extend in the X direction. The pair of movable rails 32b are attached to the pair of fixed rails 32a so as to be movable in the X direction. The pair of movable rails 32b linearly extend in the Y direction. A base 33a of the support rod 33 is attached to the pair of movable rails 32b so as to be movable in the Y direction.

Figure 4:
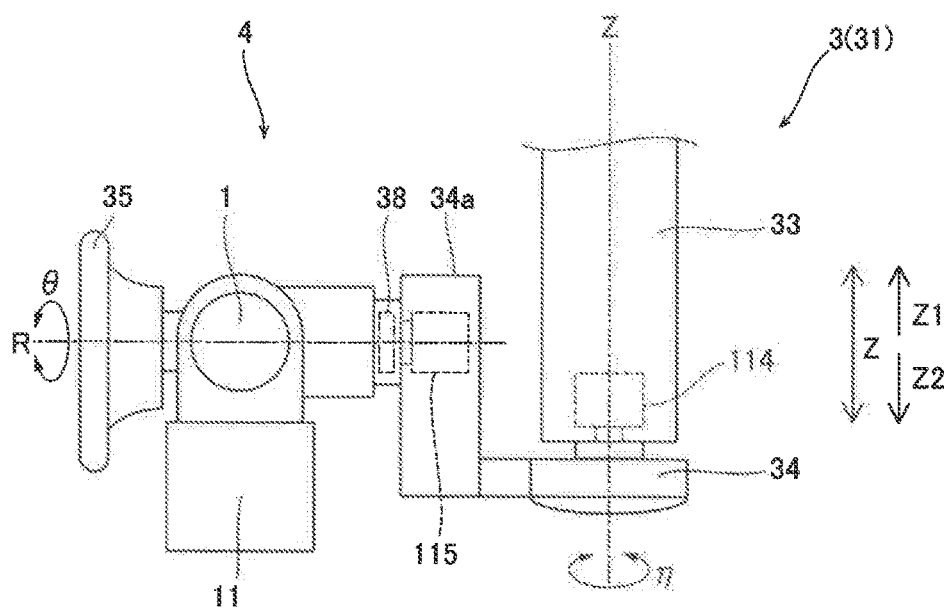
FIG. 4 is a side view schematically showing a support rod, a rotary holder, and a moving body.

As shown in FIG. 4, the support rod 33 holds the moving body 4 such that the moving body 4 can translate in the vertical direction. The support rod 33 is suspended from the base 33a (see FIG. 1) attached to the traveling mechanism 32, and is extendable in the Z direction. With these configurations, the moving mechanism 31 holds the moving body 4 such that the moving body 4 is movable in the three translational directions (X, Y, and Z directions).

The rotary holder 34 is provided at the tip (lower end) of the support rod 33. The support rod 33 supports the rotary holder 34 such that the rotary holder 34 is rotatable in the η direction about the vertical axis (Z-axis). The Z-axis coincides with the central axis of the support rod 33. The rotary holder 34 has a shape in which one end side is connected to the support rod 33 and the other end side rises upward at a position offset in the radial direction (R-axis direction) of the support rod 33. The rotary holder 34 supports the moving body 4 by an other end side holder 34a that rises upward.

At the other end side holder 34a, the rotary holder 34 holds the moving body 4 such that the moving body 4 is rotatable in the θ direction about the horizontal axis (R-axis). The R-axis is in the radial direction (horizontal direction) of the support rod 33. With these configurations, the moving mechanism 31 holds the moving body 4 such that the moving body 4 is movable in the two rotational directions (η and θ directions).

The moving mechanism 31 includes the grip 35. The grip 35 is provided on the movable body 4, and is supported by the rotary holder 34 so as to rotate integrally with the moving body 4. The grip 35 is supported by the support rod 33 so as to move integrally with the moving body 4. That is, the grip 35 is held by the support rod 33 via the rotary holder 34, and moves integrally with the moving body 4 in the plurality of directions (X, Y, Z, η, and θ). An operator can move the moving body 4 in the plurality of directions (X, Y, Z, η, and θ) by holding the grip 35 and applying a force.

In the first embodiment, the holding mechanism 3 includes a force detector 38 that detects the direction of a force applied to the moving mechanism 31 and the controller 7 that determines a direction in which movement is permitted by the switching means 36 among the plurality of directions based on the detected direction of the force. The force detector 38 is an example of a "force direction detection means" in the claims. The controller 7 is an example of a "permission direction determination means" and a "free mode setting means" in the claims. These configurations are described in detail.

<Switching Means>

Figure 5:
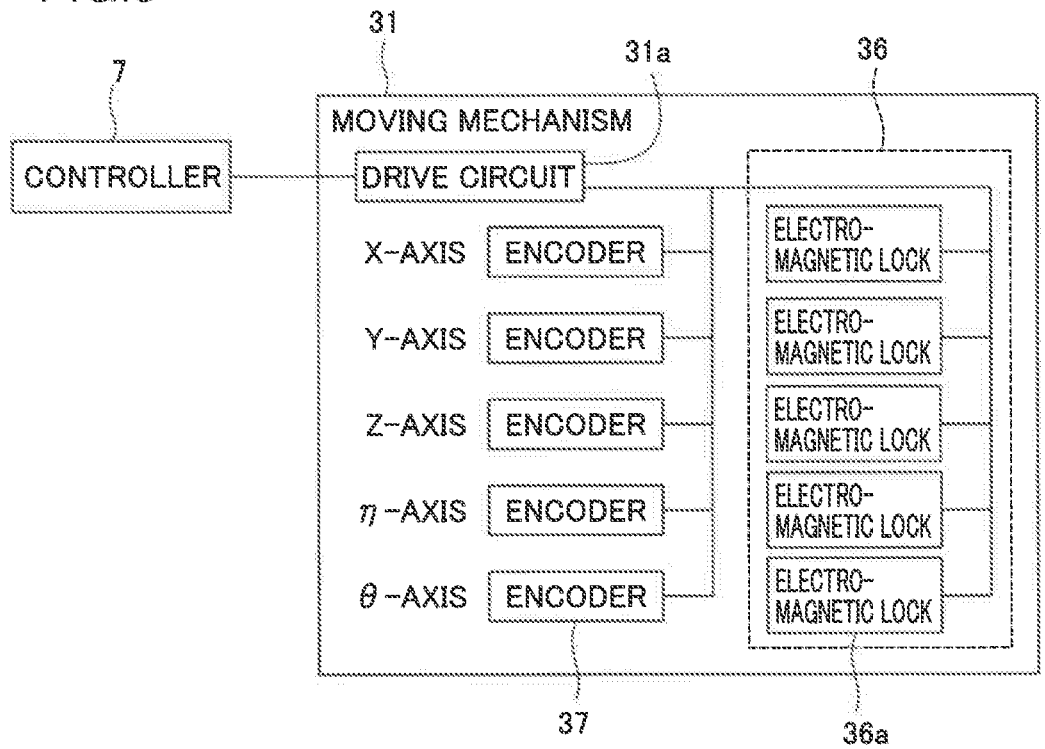
FIG. 5 is a block diagram showing an example of a switching means.

As shown in FIG. 5, the switching means 36 includes a plurality of locking mechanisms respectively corresponding to the plurality of directions and that lock movement of the moving body 4. In the first embodiment, electromagnetic locks (electromagnetic brakes) 36a are provided as the locking mechanisms. The electromagnetic locks 36a are examples of a "locking mechanism" in the claims. The locking mechanisms may be hydraulic or mechanical brakes, for example. The electromagnetic locks 36a releasably lock movement of the moving body 4 in the plurality of directions, respectively.

The electromagnetic locks 36a are individually provided in the plurality of directions, i.e. X, Y, Z, η, and θ directions. The electromagnetic locks 36a can individually switch between locking and unlocking in the X, Y, Z, η, and θ directions, respectively. Thus, the switching means 36 switches between a state of permitting movement of the moving body 4 in each of the plurality of directions (unlocking state) and a state of prohibiting movement of the moving body 4 in each of the plurality of directions (locking state).

The switching means 36 constantly maintains a state of prohibiting movement of the moving body 4 in each of the plurality of directions. Then, the switching means 36 individually switches to a state of permitting movement of the moving body 4 in the direction determined by the controller 7.

The moving mechanism 31 includes encoders 37 corresponding to respective axial directions. The encoders 37 detect the positions of the moving body 4 in the axial directions, respectively. Based on output signals from the encoders 37, the current position (the positions in the X, Y, and Z directions and the rotation angles in the η and θ directions) of the X-ray tube 1 of the moving body 4 can be obtained.

The operation of the electromagnetic locks 36a is controlled by the controller 7 via a drive circuit 31a. Furthermore, the output signals from the encoders 37 are transmitted to the controller 7 via the drive circuit 31a, and are used as operation information for operation control.

<Force Direction Detection Means>

The force detector 38 (see FIG. 2) detects the direction of the force applied to the moving mechanism 31. Specifically, the force detector 38 detects a force in each of the horizontal and vertical translational directions (X, Y, and Z directions) applied to the grip 35. In addition, the force detector 38 detects a force in each of the rotational directions (θ and η directions) about the horizontal axis (R-axis) and the vertical axis (Z-axis) applied to the grip 35.

Specifically, as shown in FIG. 4, the force detector 38 is disposed between the grip 35 and the rotary holder 34. The force detector 38 includes a component force gauge, for example. The component force gauge can detect each detection direction component of a force applied to a detection surface to measure the direction of the force and the magnitude of the force. Thus, the force detector 38 functions as a force direction detection means that detects the direction of the force applied to the moving mechanism 31.

In a configuration example shown in FIG. 4, the force detector 38 is disposed between the grip 35 and the rotary holder 34 and at a connection between the moving body 4 and the other end side holder 34a. In other words, the force detector 38 is disposed at a connection between the moving body 4 and the holding mechanism 3 (moving mechanism 31). Furthermore, the center of the detection surface of the force detector 38 is positioned on the R-axis. The detection center of the force detector 38 and the rotation center of the grip 35 are coaxial on the R-axis.

The force detector 38 is mechanically connected to the grip 35, and can detect a force in each direction applied to the grip 35. In addition, the force detector 38 can detect forces in translational directions of three orthogonal axes and moments about the three axes.

Figure 6:
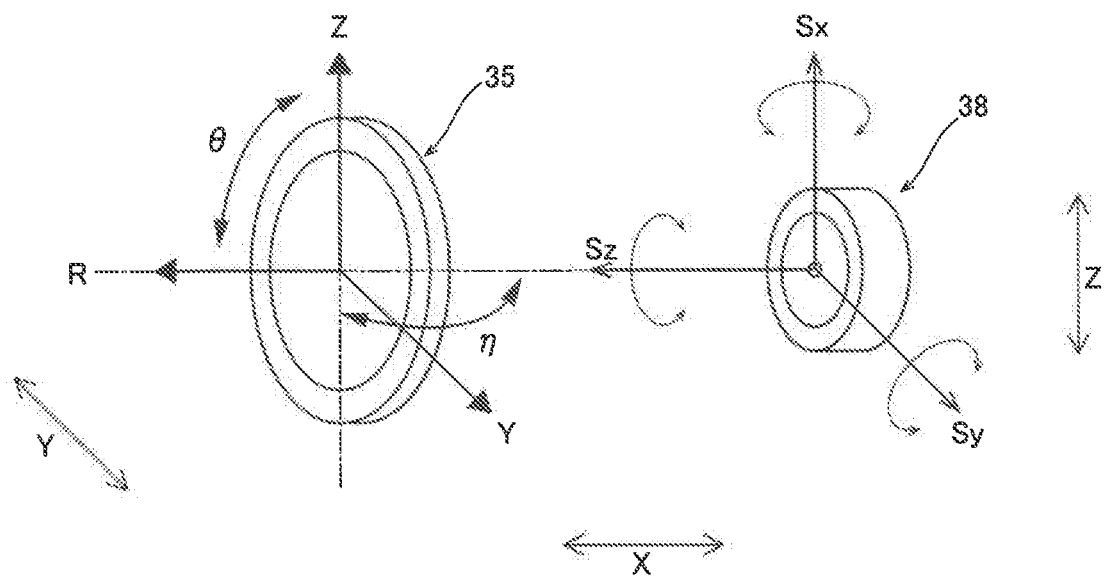
FIG. 6 is a schematic view illustrating a force detector.

Specifically, as shown in FIG. 6, the force detector 38 detects six components, e.g. forces of three axes (Sx, Sy, and Sz) and moments about the Sx-, Sy-, and Sz-axes. In FIG. 6, the Sz-axis of the force detector 38 coincides with the R-axis, and passes through the rotation center of the grip 35. Furthermore, the detection surface (Sx-Sy plane) of the force detector 38 and the front surface of the grip 35 are substantially parallel to each other. Thus, the force detector 38 detects forces for pushing the grip 35 in the directions of the Sx-, Sy-, and Sz-axes while gripping the grip 35 as forces in the Sx-, Sy-, and Sz-axial directions. The force detector 38 detects a force for rotating the grip 35 in the θ direction (about the R-axis) while gripping the grip 35 as a moment about the Sz-axis. When the Sx-axis coincides with the Z-axis in FIG. 6, the force detector 38 detects a force for rotating the grip 35 in the η direction (about the Z-axis) while gripping the grip 35 as a moment about the Sx-axis.

The detection results (the magnitudes of the forces in the translational directions of the three orthogonal axes and the magnitudes of the moments about the three axes) of the force detectors 38 are acquired by the controller 7.

<Permission Direction Determination Means>

The controller 7 acquires the directions (the η direction and the θ direction) of the moving body 4 (grip 35) based on the output signals from the encoders 37. The controller 7 acquires the forces and the moments applied in the movement directions (X, Y, Z, η, and θ) based on the directions of the moving body 4 (grip 35) and the directions (the Sx-, Sy-, and Sz-axial directions and the rotational directions about the three axes) of the forces detected by the force detector 38. Then, the controller 7 determines directions in which movement is permitted by the switching means 36 (electromagnetic locks 36a) among the plurality of directions (X, Y, Z, η, and θ) based on the detected directions of the forces. The controller 7 controls the electromagnetic locks 36a to unlock the movement in the directions of the forces detected by the force detector 38 among the plurality of directions. Thus, the controller 7 functions as a permission direction determination means that determines the directions in which movement of the moving body 4 is permitted. Therefore, the controller 7 performs automatic determination control of determining the directions in which the movement is permitted based on the directions of the forces detected by the force detector 38.

Figure 7:
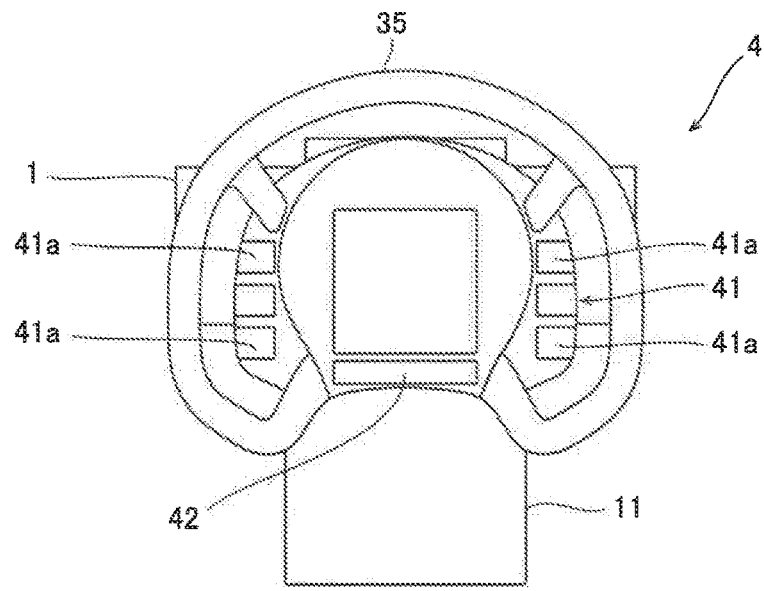
FIG. 7 is a front view of the moving body showing a grip and an operation unit.

Note that the locking state and the unlocking state can be switched by a method other than switching automatically performed when the operator applies a force to the grip 35. As shown in FIG. 7, the operation unit 41 provided on the grip 35 includes operation switches 41a that individually switch between the locking state and the unlocking state in the plurality of directions (X, Y, Z, η, and θ), respectively. The controller 7 can perform manual determination control of determining a direction in which movement of the moving body 4 is permitted based on an input operation on each operation switch. The controller 7 can individually switch the locking states and the unlocking states of the electromagnetic locks 36a in the respective directions also in the case of the manual determination control.

<Free Mode Setting Means>

In the first embodiment, the controller 7 functions as a free mode setting means that controls the electromagnetic locks 36a to permit movement of the moving body 4 in all of the plurality of directions based on a setting operation of the operator.

Specifically, as shown in FIG. 7, the operation unit 41 includes a free mode switch 42. When receiving an input operation on the free mode switch 42, the controller 7 starts control of a free mode in which all the electromagnetic locks 36a are switched to the unlocking states. In this case, the operator can freely move the moving body 4 in the plurality of directions (X, Y, Z, η, and θ) while gripping the grip 35.

When the control of the free mode is started, the controller 7 switches the electromagnetic locks 36a to a state of prohibiting the movement in all of the plurality of directions based on a setting cancellation operation of the operator or a passage of time after permission of the movement in all of the plurality of directions. The setting cancellation operation of the operator includes inputting the free mode switch 42 once to switch to the free mode and then inputting the free mode switch 42 again, and inputting a dedicated canceling switch (not shown), for example. The passage of time can be, for example, several seconds after the start of the free mode, such as five seconds.

(Automatic Determination Control)

Figure 8:
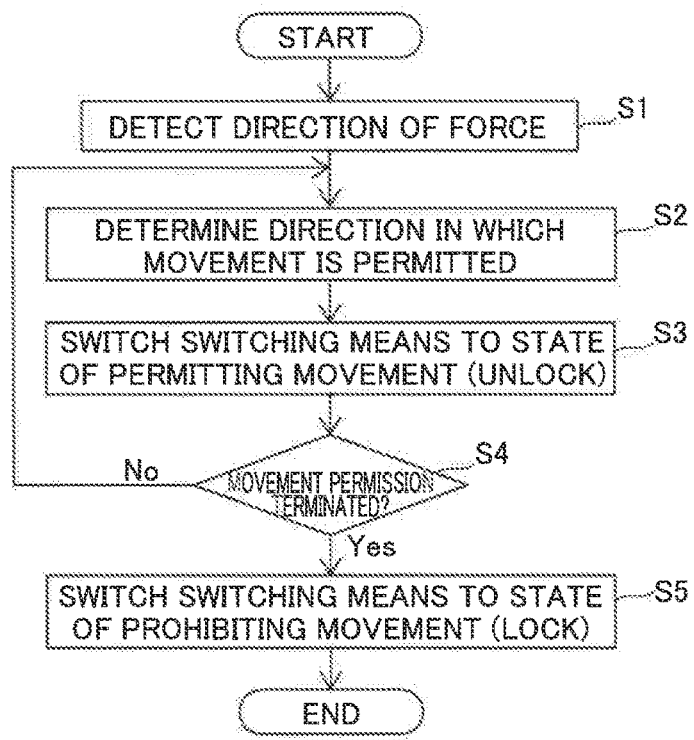
FIG. 8 is a flowchart illustrating automatic determination control according to the first embodiment.

Processing of automatic determination control performed when the moving body 4 is moved is now described with reference to FIG. 8. The control processing is performed by the controller 7. In the automatic determination control, each electromagnetic lock 36a of the moving mechanism 31 is constantly kept in the locking state unless the controller 7 switches the locking state to the unlocking state as a result of the automatic determination control.

In step S1, the controller 7 acquires the detection result of the force detector 38. When the operator grips the grip 35 and applies a force in the movement direction to move the moving body 4, the force is detected by the force detector 38. The controller 7 acquires the direction (X, Y, Z, η, or θ) of the force applied by the operator from the detection result of the force detector 38 and the detection result of the encoder 37.

In step S2, the controller 7 determines the direction in which the switching means 36 (electromagnetic lock 36a) permits the movement based on the direction of the force detected in step S1. Specifically, when forces in one or the plurality of directions (X, Y, Z, η, and θ) are detected, the controller 7 determines the detected direction(s) of the force(s) as the direction(s) (movement direction(s)) in which the movement is permitted.

In step S3, the controller 7 switches the switching means 36 to a state of permitting movement of the moving body 4 in the determined movement direction(s). That is, the controller 7 switches the electromagnetic lock(s) 36a corresponding to the determined movement direction(s) from the locking state to the unlocking state. Thus, the operator can move the moving body 4 in the detected movement direction. On the other hand, the controller 7 keeps, in the locking state, the electromagnetic lock(s) 36a corresponding to the direction(s) other than the determined movement direction (s) among the plurality of directions (X, Y, Z, η, and θ).

In step S4, the controller 7 determines whether or not the movement permission is terminated. For example, while a force is detected by the force detector 38, the controller 7 maintains the state of permitting the movement. When there is no movement direction in which the movement permission is terminated, the controller 7 repeats step S1 to step S3. When a force applied in a certain movement direction by the operator is no longer detected after the switching means 36 is switched to a state of permitting the movement in the certain movement direction, in step S2, the certain movement direction is excluded from the directions in which the movement is permitted. In this case, in step S4, the controller 7 determines that the movement permission is terminated, and advances to step S5.

In step S5, the controller 7 switches the switching means 36 to a state of prohibiting the movement in the movement direction in which the movement permission is terminated. That is, the controller 7 switches the electromagnetic lock 36a from the unlocking state to the locking state. Thereafter, the controller 7 returns to step S1.

The processing described above is repeated such that control operations for permitting the movement in the direction are realized when a force is applied by the operator.

Effects of First Embodiment

According to the first embodiment, the following effects are achieved.

According to the first embodiment, as described above, the force detector 38 that detects the direction of the force applied to the moving mechanism 31 and the controller 7 that determines the direction in which the movement is permitted by the switching means 36 among the plurality of directions (X, Y, Z, η, and θ) based on the detected direction of the force. Accordingly, when a force is applied to the moving mechanism 31 (or the moving body 4), the controller 7 can switch the switching means 36 to a state of permitting the movement in the direction in which the force is applied. Consequently, the operator can automatically switch the switching means 36 to the state of permitting the movement in a direction (movement direction) in which the operator wishes to move the moving body 4 and move the moving body 4 simply by applying a force in the movement direction without a switch operation, for example. Thus, the operability at the time of moving the moving body 4 for X-ray imaging can be improved. When the moving body 4 is aligned, it is not necessary for the operator to shift his or her gaze from the imaging position, and thus the usability can be improved.

According to the first embodiment, as described above, the force detector 38 that detects the force in the vertical direction (Z direction) applied to the grip 35 is provided. Accordingly, the operator can permit the moving body 4 to move in the vertical direction by performing an operation for moving the moving body 4 in the vertical direction while holding the grip 35 and can move and align the moving body 4 in the vertical direction while continuing the operation, and thus the operability can be further improved.

According to the first embodiment, as described above, the force detector 38 that detects the force in each of the horizontal and vertical translational directions (X, Y, and Z) applied to the grip 35 is provided. Accordingly, the operator can permit the movement in the movement direction simply by applying a force while holding the grip 35 at the time of translational movement in each of the X, Y, and Z directions and can translate the moving body 4 while continuing to apply the force, and thus the operability can be still further improved.

According to the first embodiment, as described above, the force detector 38 disposed between the grip 35 and the support rod 33 and capable of detecting the forces in three orthogonal axial directions is provided. Accordingly, the apparatus configuration can be simplified as compared with the configuration in which a force detector is individually provided for each of the three orthogonal axial directions.

According to the first embodiment, as described above, the force detector 38 that detects the force in the rotational direction (θ) about the horizontal axis (R-axis) applied to the grip 35 is provided. Accordingly, the operator can permit movement of the moving body 4 in the rotational direction about the horizontal axis by moving the grip 35 about the horizontal axis while holding the grip 35 and can align the moving body 4 while continuing to move the grip 35, and thus the operability can be further improved. Furthermore, unlike the case in which the position (operation position) of a switch or the like changes before and after the rotation about the horizontal axis such that the operability changes, and it is necessary to reconfirm the operation position, the operator can rotate the moving body 4 simply by applying a force in a direction in which the operator wishes to move the moving body 4, and thus an intuitive operation is possible regardless of the direction of the moving body 4. Also in this point, the operability is improved.

According to the first embodiment, as described above, the force detector 38 that detects the force in each of the rotational directions (θ and η) about the horizontal axis (R-axis) and the vertical axis (Z-axis) applied to the grip 35 is provided. Accordingly, in any of the rotational directions, the operator can permit rotational movement of the moving body 4 simply by applying a force while holding the grip 35 and can rotate the moving body 4 while continuing to apply the force. Consequently, the operability can be still further improved.

According to the first embodiment, as described above, the force detector 38 disposed between the grip 35 and the rotary holder 34 and capable of detecting the moments about the plurality of orthogonal axes is provided. Accordingly, the apparatus configuration can be simplified as compared with the configuration in which a force detector is individually provided for each of the rotation axes.

According to the first embodiment, as described above, the force detector 38 capable of detecting the forces in the translational directions of the three orthogonal axes and the moments about the three axes is provided. Accordingly, even in the configuration in which the moving body 4 is movable in multiple directions, the shared force detector 38 can detect the force in each of the movement directions and permit the movement. Therefore, even in the configuration in which the moving body 4 is movable in multiple directions, it is not necessary to individually provide a force detector for each of the movement directions, and thus the apparatus configuration can be extremely simplified.

According to the first embodiment, as described above, the controller 7 capable of setting a mode to the free mode in which movement of the moving body 4 in all of the plurality of directions is permitted by the electromagnetic locks 36a based on the setting operation of the operator is provided. Accordingly, after the setting operation of the operator is obtained, the moving body 4 can be shifted to the free mode in which the moving body 4 is freely movable. For example, after the moving body 4 is roughly aligned in the free mode, only position adjustment in a specific movement direction can be performed by the automatic determination control, and the usability can be still further improved.

According to the first embodiment, as described above, the controller 7 switches the switching means 36 to a state of prohibiting the movement in all of the plurality of directions based on the setting cancellation operation of the operator or the passage of time after permission of the movement in all of the plurality of directions. Accordingly, it is easy to properly and selectively use movement permission in the free mode and movement permission based on the detected direction of the force.

According to the first embodiment, as described above, the switching means 36 is constantly maintained in a state (locking state) of prohibiting movement of the moving body 4 in each of the plurality of directions (X, Y, Z, η, and θ), and is switched to a state of individually permitting movement of the moving body 4 in the direction determined by the controller 7. Accordingly, when movement of the moving body 4 in the direction of the force applied by the operator is permitted, movement of the moving body 4 in the direction not intended by the operator can be significantly reduced or prevented.

According to the first embodiment, as described above, the switching means 36 includes the plurality of electromagnetic locks 36a respectively corresponding to the plurality of directions and that lock movement of the moving body 4, and unlocks the electromagnetic lock 36a corresponding to the direction determined by the controller 7. Accordingly, the movement only in the direction determined by the controller 7 can be easily and individually permitted, and the movement in the other directions can be continuously prohibited.

Second Embodiment

An X-ray imaging apparatus according to a second embodiment of the present invention is now described with reference to FIGS. 9 to 12. In the second embodiment, a configuration example in which an assisting force is automatically applied to a moving body based on a force applied to a moving mechanism in addition to the aforementioned first embodiment is described. In the second embodiment, the same reference numerals are used for the same structures as those in the first embodiment, and description thereof is omitted.

(Configuration of X-Ray Imaging Apparatus)

Figure 9:
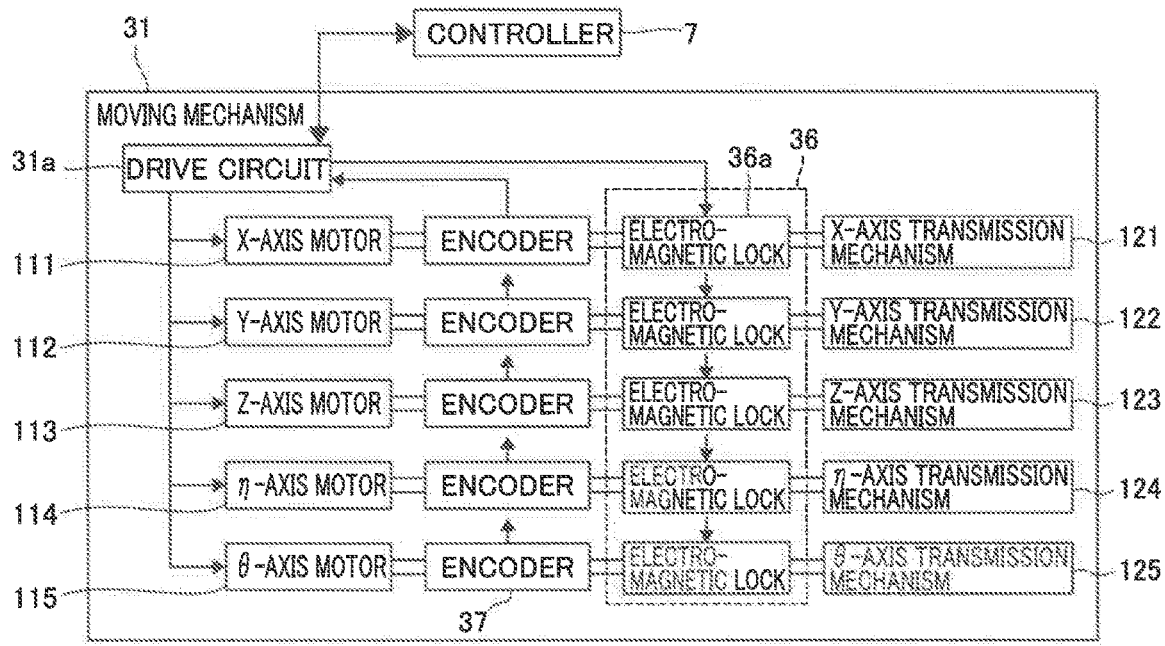
FIG. 9 is a block diagram of a moving mechanism according to the second embodiment.

In the second embodiment, a holding mechanism 3 includes a force strength detection means that detects the magnitude of a force applied to a moving mechanism 31. Furthermore, the holding mechanism 3 includes an assisting means that applies an assisting force in the movement direction of a moving body 4 to the moving body 4 based on the detected magnitude of the force. In the second embodiment, as shown in FIG. 9, an example in which the holding mechanism 3 includes a plurality of motors (111 to 115) and a controller 7 and the motors constitute the assisting means is shown.

<Force Strength Detection Means>

In the second embodiment, a force detector 38 (see FIG. 4) of the holding mechanism 3 also functions as the force strength detection means. That is, the force detector 38 that detects the direction and the magnitude of a force includes a force direction detection means and the force strength detection means that are integral and unitary with each other. The configuration of the force detector 38 is similar to that of the aforementioned first embodiment.

<Assisting Means>

Figure 10:
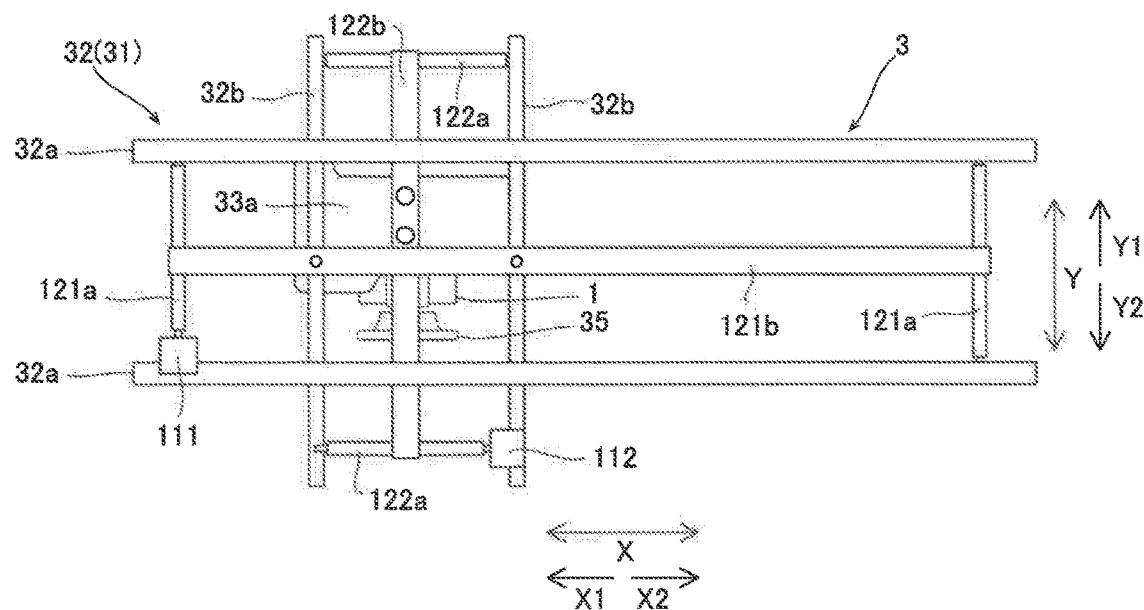
FIG. 10 is a plan view schematically showing a traveling mechanism according to the second embodiment.

A traveling mechanism 32 includes the X-axis motor 111 and an X-axis transmission mechanism 121. For example, as shown in FIG. 10, the X-axis transmission mechanism 121 is a belt-pulley mechanism including a pair of rollers (pulleys) 121a disposed in the vicinity of opposite ends of fixed rails 32a and a timing belt 121b stretched between the pair of rollers 121a. A pair of movable rails 32b are fixed to the timing belt 121b, and the X-axis motor 111 rotationally drives the rollers 121a to apply an assisting force in an X direction to the pair of movable rails 32b (moving body 4).

The traveling mechanism 32 includes the Y-axis motor 112 and a Y-axis transmission mechanism 122, as shown in FIG. 9. Similarly to the X-axis transmission mechanism 121, for example, the Y-axis transmission mechanism 122 is a belt-pulley mechanism including a pair of rollers 122a and a timing belt 122b, as shown in FIG. 10. A base 33a of a support rod 33 is fixed to the timing belt 122b, and the Y-axis motor 112 rotationally drives the rollers 122a to apply an assisting force in a Y direction to the support rod 33 (moving body 4).

As shown in FIG. 9, the support rod 33 (see FIG. 1) includes the Z-axis motor 113 and a Z-axis transmission mechanism 123. The Z-axis transmission mechanism 123 is a winding mechanism including a wire 123a (see FIG. 1) connected to a rotary holder 34 at the lower end of the support rod 33, for example. The Z-axis motor 113 is driven to wind up the wire 123a such that an assisting force in a Z direction is applied to the rotary holder 34 (moving body 4).

As shown in FIG. 9, the support rod 33 (see FIG. 4) includes the η-axis motor 114 that rotationally drives the rotary holder 34 about a Z-axis. It is not necessary to directly connect the η-axis motor 114 to the rotary holder 34, and an η-axis transmission mechanism 124 (see FIG. 9) such as a reduction gear may be provided. The η-axis motor 114 applies an assisting force in an η direction to the rotary holder 34 (moving body 4).

The rotary holder 34 (see FIG. 4) includes the θ-axis motor 115 that rotationally drives the moving body 4 about an R-axis in an other end side holder 34a. It is not necessary to directly connect the θ-axis motor 115 to the moving body 4, and a θ-axis transmission mechanism 125 (see FIG. 9) such as a reduction gear may be provided. The θ-axis motor 115 applies an assisting force in a θ direction to the moving body 4.

As shown in FIG. 9, an encoder 37 and a switching means 36 (electromagnetic lock 36a) are connected to each of the motors (the X-axis motor 111, the Y-axis motor 112, the Z-axis motor 113, the η-axis motor 114, and the θ-axis motor 115).

The operation of each motor (each of the X-axis motor 111, the Y-axis motor 112, the Z-axis motor 113, the η-axis motor 114, and the θ-axis motor 115) and the operation of each electromagnetic lock 36a are controlled by the controller 7 via a drive circuit 31a. Furthermore, an output signal from each encoder 37 is transmitted to the controller 7 via the drive circuit 31a, and is used as operation information for operation control.

The controller 7 applies an assisting force in the movement direction of the moving body 4 to the moving body 4 based on the magnitude of the force detected by the force detector 38. The controller 7 controls the motor (the X-axis motor 111, the Y-axis motor 112, the Z-axis motor 113, the η-axis motor 114, or the θ-axis motor 115) corresponding to a direction in which the assisting force is applied to be individually driven so as to generate an assisting force in the movement direction of the moving body 4.

Figure 11:
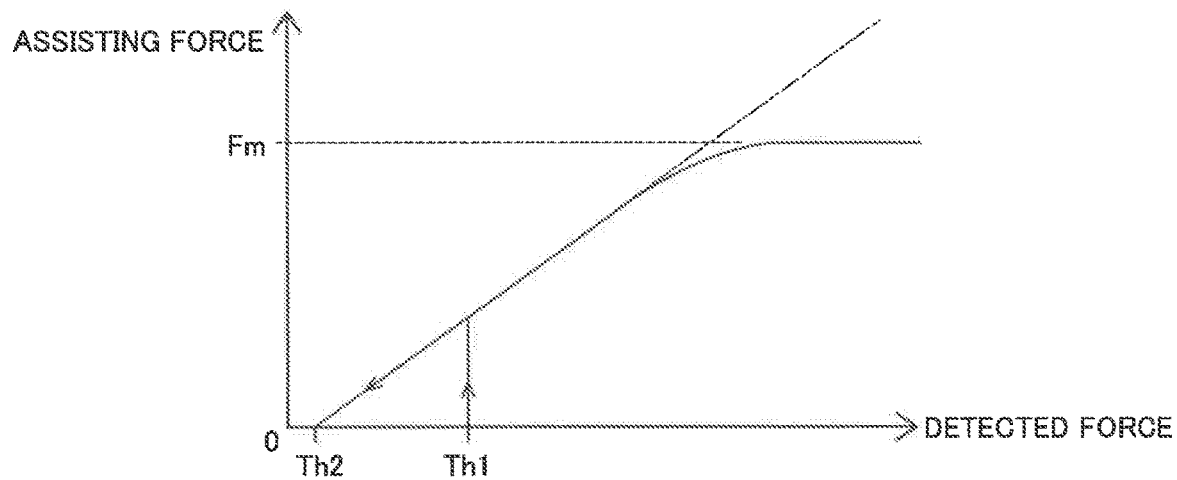
FIG. 11 is a graph showing the relationship between detected force detected by a force detector and assisting force.

Specifically, the controller 7 applies an assisting force having a magnitude according to the detected magnitude of the force to the moving body 4. For example, FIG. 11 shows an example of the relationship between the magnitude (horizontal axis) of the force (detected force) detected by the force detector 38 when an operator applies a force to a grip 35 and the generated assisting force (vertical axis).

The controller 7 controls each motor to generate a larger assisting force as the detected force increases. For example, the controller 7 controls the motor to generate an assisting force proportional to the detected force in part or all of assist control. In this case, as shown by a two-dot chain line in FIG. 11, the assisting force may be simply proportional to the detected force, or the upper limit Fm of the assisting force may be set such that the assisting force does not exceed the upper limit Fm.

For example, when a force equal to or greater than a first threshold Th1 is detected, the controller 7 may start assist control of applying an assisting force. Thus, large movement of the moving body 4 against the intention of the operator can be significantly reduced or prevented. In addition, after the start of the assist control, the controller 7 may stop the assist control of applying an assisting force when the detected force is lower than a second threshold Th2. At this time, it is preferable to make the second threshold Th2 smaller than the first threshold Th1. In this case, the operator can receive assistance until just before stopping of the heavy moving body 4, and thus the moving body 4 is easily aligned.

(Assist Control Processing)

Figure 12:
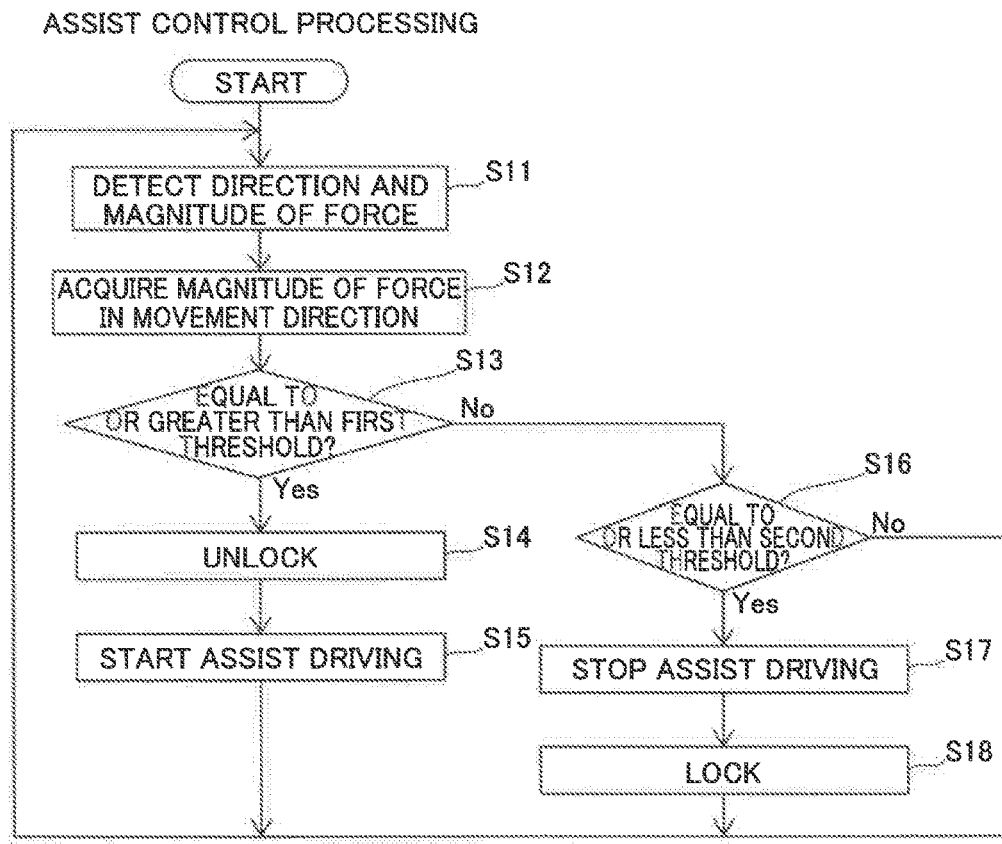
FIG. 12 is a flowchart illustrating assist control according to the second embodiment.

Assist control processing at the time of moving the moving body 4 is now described with reference to FIG. 12. The assist control processing is performed by the controller 7. Here, an example in which automatic determination processing is simultaneously performed is described.

In step S11, the controller 7 acquires the detection results (the direction and the magnitude of the force) of the force detector 38. In step S12, the controller 7 acquires the direction and the magnitude of the force applied by the operator from the detection result of the force detector 38 and the detection result of the encoder 37. Although the following processing in step S13 and the subsequent steps is performed individually for each of the plurality of directions (X, Y, Z, η, and θ), the processing for one arbitrary direction is here described for convenience.

In step S13, the controller 7 determines whether or not assistance is started based on the magnitude of the force acquired in step S12. That is, the controller 7 determines whether or not the magnitude of the force in the movement direction to be determined is equal to or greater than the first threshold Th1.

When the magnitude of the force is equal to or greater than the first threshold, the controller 7 switches the electromagnetic lock 36a corresponding to the movement direction to an unlocking state in step S14, and starts assist driving in step S15. The controller 7 drives the motor (any one of the X-axis motor 111, the Y-axis motor 112, the Z-axis motor 113, the 114-axis motor 114, and the θ-axis motor 115) corresponding to the direction in which the assisting force is applied, and generates an assisting force in the movement direction. At this time, as shown in FIG. 11, the controller 7 generates an assisting force in proportion to the magnitude of the force in the movement direction. After the start of the assistance, the processing returns to step S11.

On the other hand, in step S13, when the magnitude of the force in the movement direction to be determined is less than the first threshold Th1, the controller 7 advances to step S16.

In step S16, the controller 7 determines whether the assistance is stopped or the current state is maintained based on the magnitude of the force in the movement direction to be determined. That is, the controller 7 determines whether or not the magnitude of the force is equal to or less than the second threshold Th2. The controller 7 continues the current state when the magnitude of the force applied to the operator is not equal to or less than the second threshold Th2 (when the magnitude exceeds the second threshold Th2). That is, during the assistance (in a state in which the movement is permitted), the assistance is continued, and during stopping of the assistance (in a state in which the movement is prohibited), the assistance stop state is continued.

When the magnitude of the force is equal to or less than the second threshold Th2, the controller 7 stops the assist driving of the corresponding motor in step S17, and switches the corresponding electromagnetic lock 36a to a locking state in step S18.

The processing described above is repeated such that when a force is applied by the operator, the control operation for generating an assisting force having a magnitude corresponding to the detected magnitude of the force as well as the control operation for permitting the movement in the direction of the applied force is realized.

Effects of Second Embodiment

According to the second embodiment, similarly to the aforementioned first embodiment, the force detector 38 and the controller 7 that determines the direction in which the movement is permitted by the switching means 36 among the plurality of directions based on the detected direction of the force are provided such that the operability at the time of moving the moving body 4 for X-ray imaging can be improved.

According to the second embodiment, as described above, the force detector 38 that detects the magnitude of the force applied to the moving mechanism 31 and the controller 7 that applies an assisting force in the movement direction of the moving body 4 to the moving body 4 based on the detected magnitude of the force are provided. Accordingly, the force applied to the moving mechanism 31 by the operator is detected such that not only permission of movement of the moving body 4 but also power assistance for movement can be performed. Consequently, the operability can be significantly improved.

According to the second embodiment, as described above, the force detector 38 that detects the force in the vertical direction (Z direction) applied to the grip 35 is provided. Accordingly, the operator simply moves the moving body 4 in the vertical direction while holding the grip 35 such that power assistance can be performed, and thus the operability can be further improved.

According to the second embodiment, as described above, the force detector 38 that detects the force in each of the horizontal and vertical translational directions (X, Y, and Z directions) applied to the grip 35 is provided. Accordingly, power assistance in each direction can be started by the common operation in which the operator simply applies a force in the movement direction while holding the grip 35, and thus the operability can be still further improved.

According to the second embodiment, as described above, the force detector 38 that detects the force in the rotational direction (θ direction) about the horizontal axis applied to the grip 35 is provided. Accordingly, the operator simply rotates the grip 35 about the horizontal axis such that power assistance can be performed, and thus the operability can be further improved.

According to the second embodiment, as described above, the force detector 38 that detects the force in each of the rotational directions (η and θ directions) about the horizontal axis and the vertical axis applied to the grip 35 is provided. Accordingly, power assistance can be started by the common operation of simply applying a force in the rotational movement direction, and thus the operability can be still further improved.

According to the second embodiment, as described above, the force detector 38 that detects the direction of the force and the magnitude of the force includes the force direction detection means and the force strength detection means that are integral and unitary with each other. Accordingly, the apparatus configuration can be simplified as compared with the configuration in which the direction of the force and the magnitude of the force are detected by separate detectors.

According to the second embodiment, as described above, the controller 7 applies, to the moving body 4, an assisting force having a magnitude corresponding to the detected magnitude of the force. Accordingly, an assisting force is increased as a force applied by the operator is increased such that the moving body 4 can be easily (lightly) moved. Therefore, even a heavy moving body 4 can be quickly moved, and thus the usability in X-ray imaging can be further improved.

Third Embodiment

An X-ray imaging apparatus according to a third embodiment of the present invention is now described with reference to FIG. 13. In the third embodiment, a configuration example in which an operator detection means is provided to permit movement of a moving body 4 when an operator is detected in addition to the aforementioned second embodiment is described. In the third embodiment, the same reference numerals are used for the same structures as those in the second embodiment, and description thereof is omitted.

(Configuration of X-Ray Imaging Apparatus)

Figure 13:
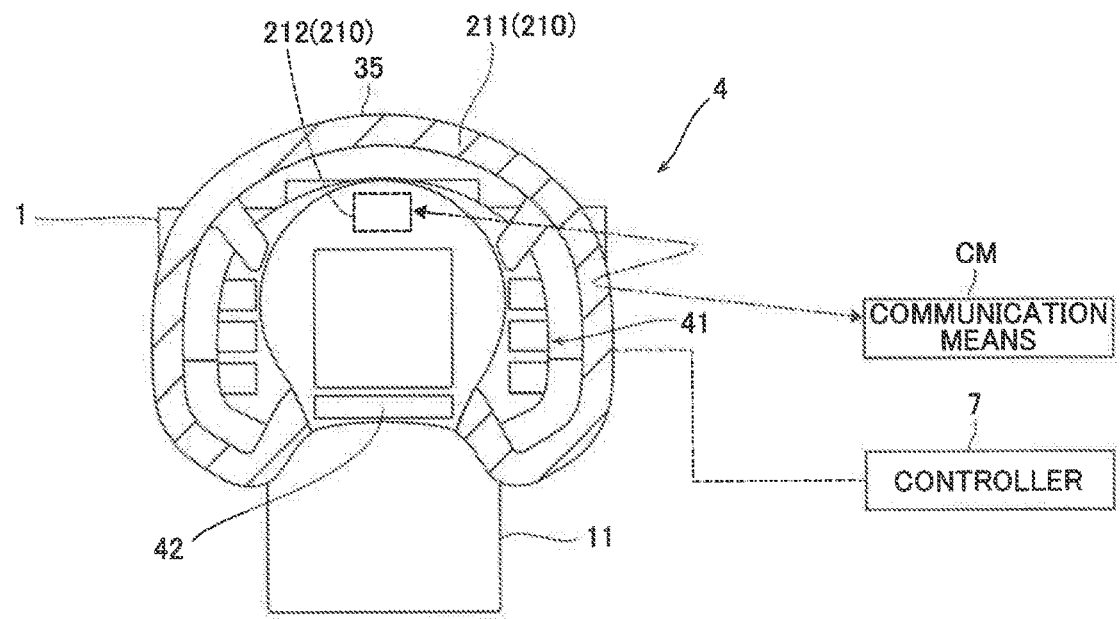
FIG. 13 is a schematic view illustrating an operator detection means according to the third embodiment.

In the third embodiment, as shown in FIG. 13, the X-ray imaging apparatus 100 (holding mechanism 3) further includes an operator detection means 210 that detects the operator. The operator detection means 210 includes a contact sensor 211 that detects that a grip 35 is gripped by the operator, for example. As the contact sensor 211, sensors using various methods such as a capacitance sensor and a piezoelectric sensor using a piezoelectric film can be used. The contact sensor 211 is provided over a predetermined range in the grip 35, for example, and detects contact of the operator's finger with the grip 35. FIG. 13 shows an example in which the contact sensor 211 is provided over substantially the entire grip 35 (a hatched portion in FIG. 13).

The operator detection means 210 is a communicator 212 capable of wireless communication with a communication means CM held by the operator, for example. The communicator 212 is provided in the grip 35 and an operation unit 41, for example, and performs bi-directional communication with the communication means CM via near field communication. The communication means CM is a communication device carried by the operator, an authentication terminal capable of communication, or another device. A controller 7 can detect the operator via the communicator 212. In the bi-directional communication, authentication information of the operator may be included in the communication contents, and personal authentication may be performed. Although both the contact sensor 211 and the communicator 212 are illustrated for convenience in FIG. 13, only one of the contact sensor 211 and the communicator 212 may be provided.

When the operator is not detected by the operator detection means 210, the controller 7 controls a switching means 36 (electromagnetic lock 36a) to prohibit movement of the moving body 4. When the operator is detected by the operator detection means 210, the controller 7 determines a direction in which the movement is permitted by the switching means 36 (electromagnetic lock 36a). That is, when a force in the movement direction is detected by a force detector 38 in a state in which the operator is detected, the controller 7 switches the electromagnetic lock 36a corresponding to the movement direction to an unlocking state.

Effects of Third Embodiment

According to the third embodiment, similarly to the aforementioned first embodiment, the force detector 38 and the controller 7 that determines the direction in which the movement is permitted by the switching means 36 among a plurality of directions based on the detected direction of the force are provided such that the operability at the time of moving the moving body 4 for X-ray imaging can be improved.

According to the third embodiment, as described above, the operator detection means 210 that detects the operator is provided, and the controller 7 controls the switching means 36 to prohibit the movement when the operator is not detected by the operator detection means 210, and determines the direction in which the movement is permitted by the switching means 36 when the operator is detected.

Accordingly, even in the configuration in which movement of the moving body 4 is automatically permitted based on the applied force, permission of the movement (movement of the moving body 4) not intended by the operator can be prevented.

According to the third embodiment, as described above, the operator detection means 210 (contact sensor 211) that detects that the grip 35 is gripped by the operator is provided. Accordingly, using the fact that the operator grips the grip 35 when moving the moving body 4, the operator can be easily and reliably detected.

According to the third embodiment, as described above, the communicator 212 capable of wireless communication with the communication means CM held by the operator is provided, and the controller 7 detects the operator via the communicator 212. Accordingly, when the operator approaches while carrying the communication means CM in order to move the moving body 4, the operator can be easily detected. Furthermore, when the authentication information is included in the communication between the communication means CM and the communicator 212, personal authentication of the operator becomes possible, and an operation performed by an unauthorized third party can be prevented.

Fourth Embodiment

An X-ray imaging apparatus according to a fourth embodiment of the present invention is now described with reference to FIGS. 2 and 14. In the fourth embodiment, a configuration example in which a moving mechanism 31 includes an engagement means 310 to stop movement of a moving body 4 at a predetermined position in addition to the aforementioned second embodiment is described. In the fourth embodiment, the same reference numerals are used for the same structures as those in the second embodiment, and description thereof is omitted.
(Configuration of X-Ray Imaging Apparatus)

In the fourth embodiment, as shown in FIG. 2, the moving mechanism 31 includes the engagement means 310 that releasably engages with the moving mechanism 31 to stop the moving body 4 at the predetermined position. As shown in FIG. 14, the engagement means 310 includes a stopper mechanism 311 provided on the moving side and an engaging portion 321 provided on the fixed side. The engagement means 310 can be provided for each of movement mechanisms in a plurality of directions (X, Y, Z, η, and θ).

Figure 14:
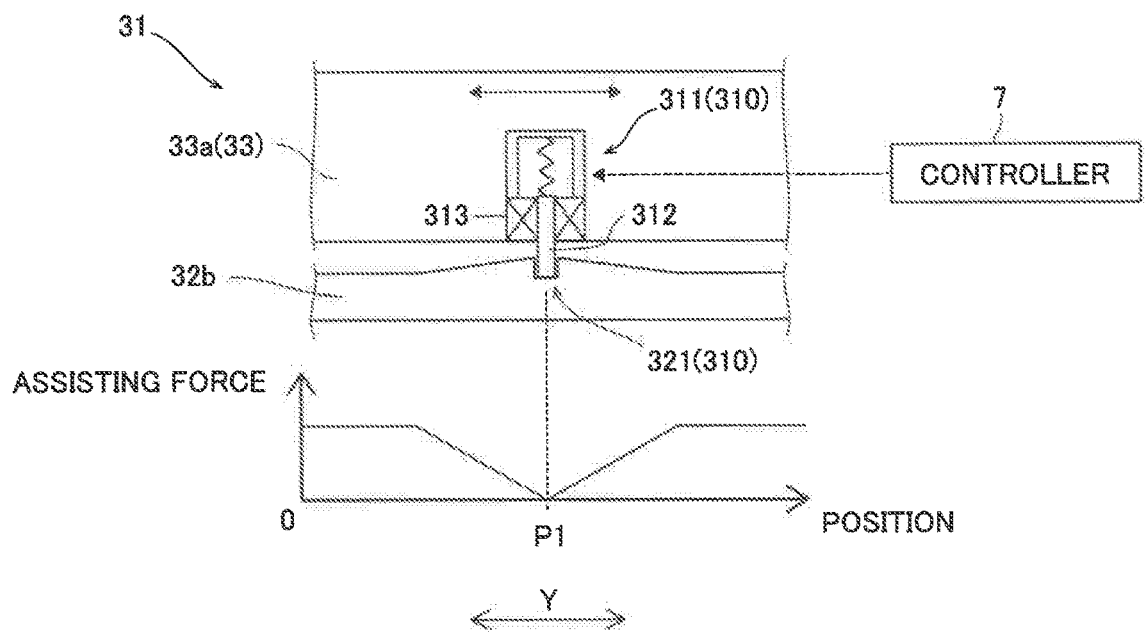
FIG. 14 is a schematic view illustrating an engagement means according to the fourth embodiment.

For example, FIG. 14 shows a configuration example of the engagement means 310 for movement of a base 33a in the Y direction with respect to a movable rail 32b. In this case, the base 33a of a support rod 33 moves with respect to the movable rail 32b, and thus the movable rail 32b is on the fixed side, and the base 33a is on the moving side. In the movable rail 32b, the engaging portion 321 is provided at a predetermined position P1. The engaging portion 321 is an engagement hole, for example. On the other hand, the base 33a includes the stopper mechanism 311 that can engage with the engaging portion 321. The stopper mechanism 311 is a solenoid pin that can move back and forth with respect to the engagement hole, for example. In the stopper mechanism 311, a pin 312 is urged toward the engagement hole, and when the base 33a moves in the Y direction and reaches the predetermined position P1, the pin 312 enters the inside of the engaging portion 321, the base 33a is stopped. Consequently, movement of the moving body 4 in the Y direction is stopped at the predetermined position P1. A controller 7 can disengage the stopper mechanism 311 from the engaging portion 321 by driving a solenoid 313 of the stopper mechanism 311 to pull in the pin 312.

The predetermined position P1 is set to a position that serves as the reference position of an X-ray tube 1 at the time of X-ray imaging. Specifically, for example, a reference position for imaging in the recumbent position (see FIG. 1) is a position at which the X-ray tube 1 is disposed on the centerline of an X-ray detector 2 provided on an imaging table 5 in the X and Y directions. In the Z direction, the reference position for imaging in the recumbent position is a position at which a distance (SID) between the focal point of the X-ray tube 1 and the detection surface of the X-ray detector 2 is a predetermined reference distance. In the η direction, the reference position for imaging in the recumbent position is an angular position at which an R-axis coincides with the Y direction, and in the θ direction, the reference position for imaging in the recumbent position is an angular position at which the optical axis of an X-ray (the direction of a collimator 11) coincides with a downward direction of the Z direction. Therefore, when the moving body 4 is moved to the predetermined position (reference position), the moving body 4 is placed at the predetermined position by an engagement means (not shown) provided on each of a fixed rail 32a (X direction), the movable rail 32b (Y direction), the support rod 33 (Z and η directions), and an other end side holder 34a (θ direction).

In the fourth embodiment, a switching means 36 (electromagnetic lock 36a) switches to a state of prohibiting movement of the moving body 4 when the moving mechanism 31 engages with the engagement means 310. That is, when movement of the moving body 4 is stopped by the engagement means 310 in each movement direction, the controller 7 switches the corresponding electromagnetic lock 36a to a locking state.

Then, when the moving body 4 is moved from the predetermined position P1, the controller 7 determines a direction in which the movement is permitted by the electromagnetic lock 36a, and disengages the moving mechanism 31 from the engagement means 310.

In the fourth embodiment, when the moving body 4 moves toward the predetermined position P1, the controller 7 decreases an assisting force to be applied to the moving body 4 as the moving body 4 is closer to the predetermined position P1. For example, as shown in FIG. 14, in the fourth embodiment, when the movement direction is a direction toward the predetermined position P1, the controller 7 decreases an assisting force with a decrease in a distance between the current position and the predetermined position P1. The controller 7 may control an assisting force to be proportional to the distance between the current position and the predetermined position P1 with a negative inclination, as shown in FIG. 14, or may control an assisting force to be inversely proportional to the distance.

Thus, as the moving body 4 is closer to the predetermined position P1, the resistance at the time of moving the moving body 4 increases, and the speed of the moving body 4 moved by an operator naturally decreases.

Effects of Fourth Embodiment

According to the fourth embodiment, similarly to the aforementioned first embodiment, a force detector 38 and the controller 7 that determines the direction in which the movement is permitted by the switching means 36 based on the detected direction of the force are provided such that the operability at the time of moving the moving body 4 for X-ray imaging can be improved.

According to the fourth embodiment, as described above, the engagement means 310 that releasably engages with the moving mechanism 31 to stop the moving body 4 at the predetermined position P1 is provided. Furthermore, the controller 7 determines the direction in which the movement is permitted by the switching means 36, and disengages the moving mechanism 31 from the engagement means 310. Accordingly, the engagement means 310 can easily and quickly position the moving body 4. Furthermore, even when the engagement means 310 is provided, the operator simply applies a force to the moving mechanism 31 such that the engagement means 310 can be disengaged, and thus the operability can be improved while positioning of the moving body 4 is facilitated.

According to the fourth embodiment, as described above, the controller 7 decreases an assisting force to be applied to the moving body 4 as the moving body 4 is closer to the predetermined position P1 when the moving body 4 moves toward the predetermined position P1. Accordingly, even when power assistance is performed, the moving body 4 is made less likely to move (the assisting force is decreased) as the moving body 4 is closer to the predetermined position P1 such that the moving speed can be reduced, and thus the shock at the time of engaging the engagement means 310 and the moving body 4 at the predetermined position P1 can be mitigated.

Fifth Embodiment

An X-ray imaging apparatus according to a fifth embodiment of the present invention is now described with reference to FIGS. 2 and 15. In the fifth embodiment, a configuration example in which whether to automatically or manually perform control of determining a direction in which the movement is permitted is switched according to an imaging method or an imaging site in addition to the aforementioned second embodiment is described. In the fifth embodiment, the same reference numerals are used for the same structures as those in the second embodiment, and description thereof is omitted.

(Configuration of X-Ray Imaging Apparatus)

In the fifth embodiment, a controller 7 switches control related to movement of a moving body 4. Specifically, the controller 7 switches between automatic determination control of determining the direction in which the movement is permitted based on the detected direction of a force and manual determination control of determining the direction in which the movement is permitted based on an operation input by an operator.

As shown in FIG. 2, a storage 8 stores, in advance, a plurality of pieces of preset information (8a and 8b) about the imaging method and the imaging site. The imaging method includes imaging in the recumbent position, imaging in the upright position, and general imaging, for example. The imaging method may include a method other than the imaging in the recumbent position, the imaging in the upright position, and the general imaging. The imaging site is a site to be imaged in X-ray imaging, and includes various anatomical sites such as a chest, an upper arm, a finger, a clavicle, and a cervical spine. The imaging method and the imaging site can be selected by the operator operating an input 9. Furthermore, in the storage 8, imaging conditions are set in advance for each of the imaging method and the imaging site. The imaging method or both the imaging method and the imaging site are set such that the position of the moving body 4 (X-ray tube 1) at the time of imaging can be roughly specified. The storage 8 stores preset information 8c about a reference position at the time of performing X-ray imaging for each imaging method and each imaging site.

Figure 15:
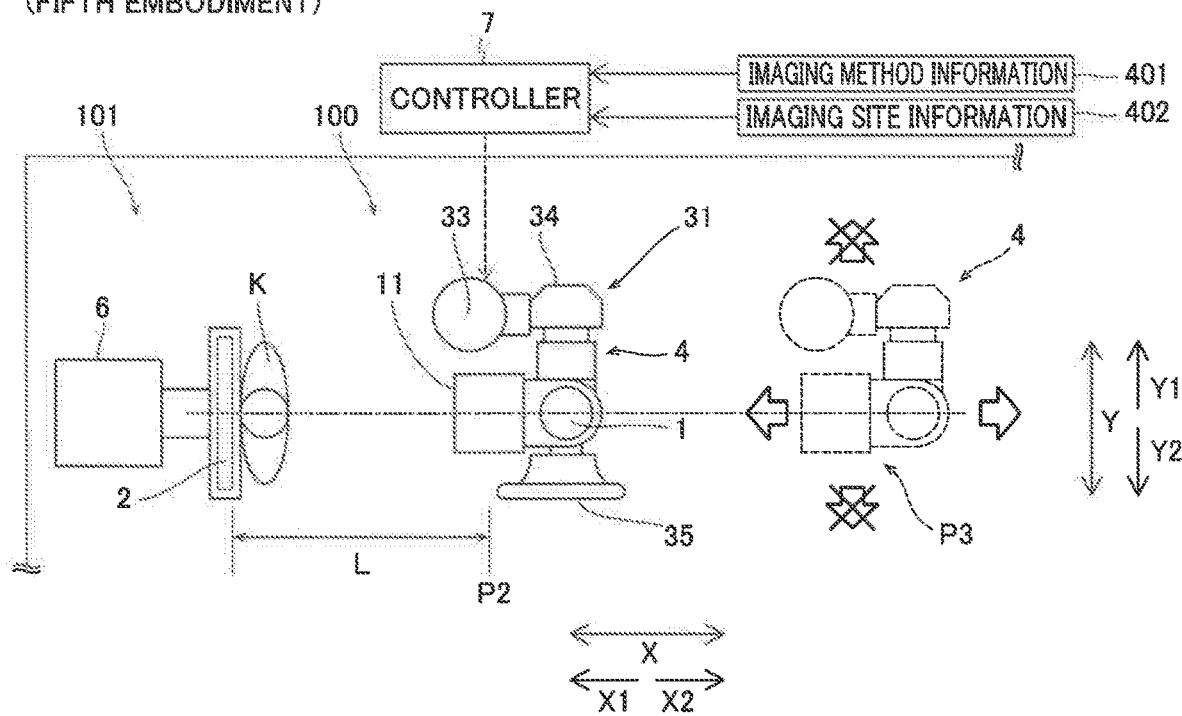
FIG. 15 is a schematic view illustrating automatic determination control according to the fifth embodiment.

As shown in FIG. 15, the controller 7 acquires imaging method information 401 and imaging site information 402 (information about the selected imaging method and imaging site) selected via the input 9. The controller 7 switches between the automatic determination control and the manual determination control according to the imaging method information 401. In addition, the controller 7 switches between the automatic determination control and the manual determination control according to the imaging site information 402 (selected imaging site).

<Control Based on Imaging Method>

The controller 7 performs the automatic determination control when the acquired imaging method information 401 is a predetermined imaging method. Thus, the operator can unlock a switching means 36 (electromagnetic lock 36a) and move the moving body 4 simply by applying a force in a direction in which the operator wishes to move the moving body 4 while gripping a grip 35.

The controller 7 performs the manual determination control without performing the automatic determination control when the acquired imaging method information 401 is other than the predetermined imaging method. In this case, the controller 7 unlocks the switching means 36 (electromagnetic lock 36a) corresponding to the movement direction designated by the operator in response to an input operation on an operation unit 41.

In the fifth embodiment, the controller 7 preferably acquires the reference position P2 of the moving body 4 in the predetermined imaging method. The reference position P2 is acquired based on the preset information 8c related to the reference position of the storage 8. Then, as shown in FIG. 15, in the automatic determination control, the controller 7 permits movement of the moving body in the movement direction in which the current position P3 of the moving body 4 is different from the reference position P2 among a plurality of directions, based on the detected direction of the force, and prohibits movement of the moving body 4 in the movement direction in which the current position P3 of the moving body 4 coincides with the reference position P2 among the plurality of directions. For example, when the predetermined imaging method is imaging in the upright position, the reference position P2 is a position spaced apart from an imaging stand 6 by a predetermined distance in the front direction (X direction).

<Control Based on Imaging Site>

The controller 7 performs the automatic determination control when the imaging site information 402 is a predetermined imaging site, and performs the manual determination control when the imaging site information 402 is other than the predetermined imaging site. For example, when the predetermined imaging site is a finger and the acquired imaging site information 402 is the finger, the controller 7 performs the automatic determination control.

In the fifth embodiment, the controller 7 preferably acquires the reference position P2 of the moving body 4 at the predetermined imaging site. Then, in the automatic determination control, the controller 7 permits movement of the moving body 4 in the movement direction in which the current position P3 of the moving body 4 is different from the reference position P2 among the plurality of directions, based on the detected direction of the force, and prohibits movement of the moving body 4 in the movement direction in which the current position P3 of the moving body 4 coincides with the reference position P2 among the plurality of directions.

For example, it is assumed that the predetermined imaging method is imaging in the upright position and the predetermined imaging site is a chest. In this case, as shown in FIG. 15, the reference position P2 is a position spaced apart from the imaging stand 6 by a predetermined distance L in the front direction (X direction). In the Z direction, the reference position is not set because there are individual differences in height.

For example, when a position shown by broken lines in FIG. 15 is the current position P3 of the moving body 4, the position in a Y direction coincides with the reference position P2 (the front of the imaging stand 6; on a one-dot chain line), but the position in the X direction is different from the reference position P2. Therefore, the controller 7 prohibits the movement in the Y direction and permits the movement in the X direction. That is, even when a force in the Y direction is detected, the controller 7 keeps the electromagnetic lock 36a corresponding to the Y direction in a locking state. On the other hand, when a force in the X direction is detected, the electromagnetic lock 36a corresponding to the X direction is switched to an unlocking state, the movement is permitted, and assist control is started.

Effects of Fifth Embodiment

According to the fifth embodiment, similarly to the aforementioned first embodiment, a force detector 38 and the controller 7 that determines the direction in which the movement is permitted by the switching means 36 are provided such that the operability at the time of moving the moving body 4 for X-ray imaging can be improved.

According to the fifth embodiment, as described above, the controller 7 switches between the automatic determination control and the manual determination control according to the imaging method information 401. Accordingly, depending on the type of imaging method, control switching can be made such that the automatic determination control is performed for a predetermined imaging method that requires movement of the moving body 4 in an arbitrary direction, and the manual determination control is performed for another imaging method that does not require the movement in the arbitrary direction, for example. Consequently, control of determining the direction in which movement of the moving body 4 is permitted can be properly and selectively used according to the purpose of the operator, and thus the usability can be further improved.

According to the fifth embodiment, as described above, in the automatic determination control, the controller 7 permits movement of the moving body 4 in the movement direction in which the current position P3 of the moving body 4 is different from the reference position P2 among the plurality of directions, based on the detected direction of the force, and prohibits movement of the moving body 4 in the movement direction in which the current position P3 of the moving body 4 coincides with the reference position P2. Accordingly, even when the automatic determination control is performed, the moving body 4 can be easily moved to the reference position P2 set according to the imaging method.

According to the fifth embodiment, as described above, the controller 7 switches between the automatic determination control and the manual determination control according to the imaging site information 402. Accordingly, depending on the imaging site, control switching can be made such that the automatic determination control is performed for a predetermined imaging site that requires movement of the moving body 4 in an arbitrary direction, and the manual determination control is performed for an imaging site that does not require the movement in the arbitrary direction, for example. Consequently, control of determining the direction in which movement of the moving body 4 is permitted can be properly and selectively used according to the purpose of the operator, and thus the usability can be further improved.

According to the fifth embodiment, as described above, in the automatic determination control, the controller 7 permits movement of the moving body 4 in the movement direction in which the current position P3 of the moving body 4 is different from the reference position P2 among the plurality of directions, based on the detected direction of the force, and prohibits movement of the moving body 4 in the movement direction in which the current position P3 of the moving body 4 coincides with the reference position P2. Accordingly, even when the automatic determination control is performed, the moving body 4 can be easily moved to the reference position P2 set according to the imaging site.

Modified Examples

The embodiments disclosed this time must be considered as illustrative in all points and not restrictive. The scope of the present invention is not shown by the above description of the embodiments but by the scope of claims for patent, and all modifications (modified examples) within the meaning and scope equivalent to the scope of claims for patent are further included.

For example, the configurations shown in the first to fifth embodiments may be combined with each other. Therefore, one or a plurality of the third to fifth embodiments may be combined with the first embodiment or the second embodiment. All the configurations of the first to fifth embodiments may be combined.

While an example of the ceiling-suspended X-ray imaging apparatus 100 (ceiling-suspended holding mechanism) has been shown in each of the aforementioned embodiments, the present invention is not restricted to this. According to the present invention, a configuration other than the ceiling-suspended type may be used. For example, as shown in a modified example of FIG. 16, the present invention may be applied to a floor traveling X-ray imaging apparatus 500 (a floor traveling holding mechanism 503).

Figure 16:
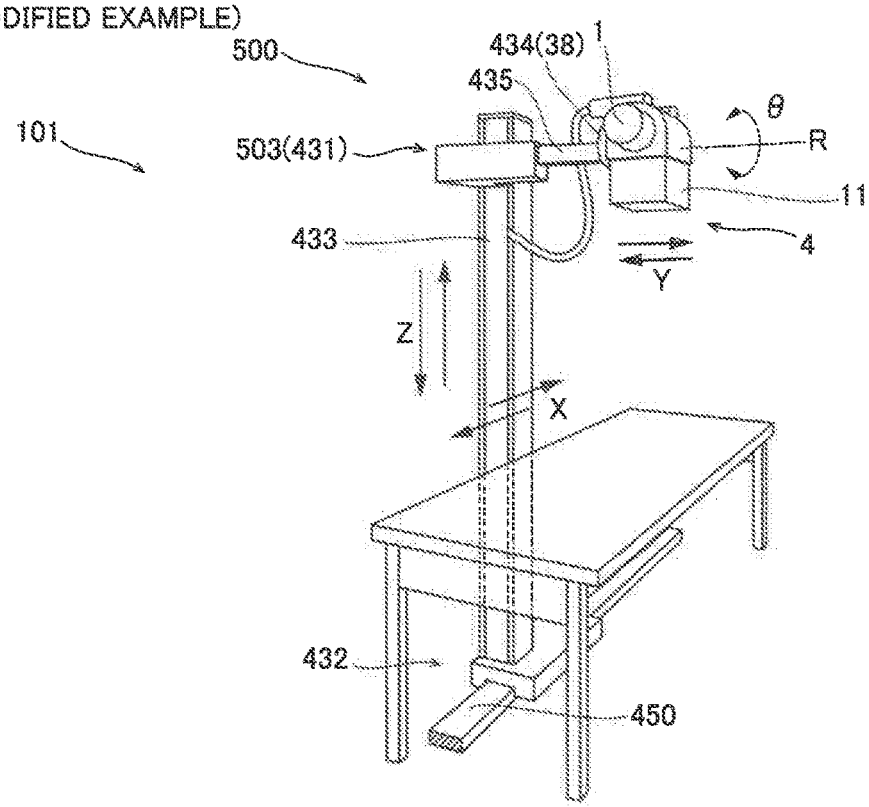
FIG. 16 is a schematic perspective view showing a modified example of the first embodiment.

In the X-ray imaging apparatus 500 (holding mechanism 503) shown in FIG. 16, a moving body 4 is supported by the holding mechanism 503 disposed on the floor surface of a imaging room 101. In FIG. 16, a moving mechanism 431 of the holding mechanism 503 includes a traveling mechanism 432 that travels in an X direction on a rail 450 on the floor, a support rod 433 that extends upward from the traveling mechanism 432, and an arm 435 attached to the support rod 433 so as to be movable in a Z direction. The arm 435 is extensible and contractible in the X direction, and supports the moving body 4 via a rotary holder 434 at its tip. The rotary holder 434 supports the moving body 4 such that the moving body 4 is rotatable in a θ direction about an R-axis. The moving body 4 includes an X-ray tube 1 and a collimator 11. The present invention may be applied to the X-ray imaging apparatus 500 (holding mechanism 503) having such a configuration, and a force detector 38 and a controller 7 that determines the direction of unlocking by a switching means 36 based on the detected direction of a force may be provided.

Besides, the present invention may be applied to a cart-type X-ray imaging apparatus (holding mechanism) including wheels, for example.

While the example in which the moving body 4 includes the X-ray tube 1 has been shown in each of the aforementioned first to fifth embodiments, the present invention is not restricted to this. According to the present invention, the moving body 4 may include the X-ray detector 2, and the moving mechanism that moves the X-ray detector may determine the unlocking direction based on the detected direction of the force.

While the example in which the moving mechanism 31 holds the moving body 4 such that the moving body 4 is movable in the plurality of directions, i.e. the five axial directions (X, Y, Z, η, and θ) has been shown in each of the aforementioned first to fifth embodiments, the present invention is not restricted to this. According to the present invention, as long as the moving mechanism holds the moving body such that the moving body is movable in a plurality of directions, the moving body may be movable in a plurality of directions other than the five directions.

While the example in which the moving mechanism 31 includes a gantry mechanism of the three orthogonal axes (X, Y, and Z) and a rotation mechanism about the three orthogonal axes has been shown in each of the aforementioned first to fifth embodiments, the present invention is not restricted to this. The moving mechanism that moves the moving body may have any structure. For example, the moving mechanism may include an articulated arm, and the moving body may be moved due to rotation at each joint and extension and contraction of the arm between the joints.

While the example in which the component force gauge capable of detecting six components of forces in the three orthogonal axes (X, Y, and Z) and moments about the three axes is provided as the force detector 38 has been shown in each of the aforementioned first to fifth embodiments, the present invention is not restricted to this. According to the present invention, a force detector other than the component force gauge may be provided. The force detector may be of a pressure measurement type such as an air pressure or liquid pressure measurement type, or of a type using the elasticity of a spring, for example, or a magnetostrictive load cell, a strain gauge, or the like may be used as the force detector.

While the example in which one force detector 38 detects forces in the plurality of directions has been shown in each of the aforementioned first to fifth embodiments, the present invention is not restricted to this. According to the present invention, a plurality of force detectors may be provided. For example, a force detector may be provided for each movable axial direction. That is, in each of the transmission mechanisms 121 to 125 shown in FIG. 5, a force detector that detects the force in the movement direction may be provided.

DESCRIPTION OF REFERENCE NUMERALS

1: X-ray tube
2: X-ray detector
3, 503: holding mechanism (holding mechanism for an X-ray imaging apparatus)
4: moving body
7: controller (permission direction determination means, assisting means, free mode setting means)
31: moving mechanism
32: traveling mechanism
33: support rod
34: rotary holder
35: grip
36: switching means
36a: electromagnetic lock (locking mechanism)
38: force detector (force direction detection means, force strength detection means)
42: free mode switch (free mode setting means)
100, 500: X-ray imaging apparatus
210: operator detection means
212: communicator
310: engagement means
401: imaging method information
402: imaging site information

The invention claimed is:

1. A holding mechanism for an X-ray imaging apparatus, the holding mechanism comprising:
a moving mechanism that holds a moving body including an X-ray tube or an X-ray detector such that the moving body is movable in a plurality of directions;
a switching means that switches between a state of permitting movement of the moving body and a state of prohibiting the movement in each of the plurality of directions;
a force direction detection means that detects a direction of a force applied to the moving mechanism; and
a permission direction determination means that determines a direction in which the movement is permitted by the switching means among the plurality of directions based on a detected direction of the force, wherein the permission direction determination means:
acquires imaging method information selected from two or three options among imaging in an upright position, imaging in a recumbent position, and general imaging; and
switches, according to the imaging method information, between automatic determination control of determining the direction in which the movement is permitted based on the detected direction of the force and manual determination control of determining the direction in which the movement is permitted based on an operation input by an operator.

2. The holding mechanism for an X-ray imaging apparatus according to claim 1, wherein
the plurality of directions include horizontal and vertical translational directions orthogonal to each other;
the moving mechanism includes a support rod that holds the moving body such that the moving body is translatable in a vertical direction, and a grip supported by the support rod such that the grip moves integrally with the moving body; and
the force direction detection means detects a force in the vertical direction applied to the grip.

3. The holding mechanism for an X-ray imaging apparatus according to claim 2, wherein
the moving mechanism includes a traveling mechanism that supports the support rod such that the support rod is translatable in a horizontal direction; and
the force direction detection means detects forces in the horizontal and vertical translational directions applied to the grip.

4. The holding mechanism for an X-ray imaging apparatus according to claim 3, wherein the force direction detection means includes a force detector disposed between the grip and the support rod and capable of detecting forces in three orthogonal axial directions.

5. The holding mechanism for an X-ray imaging apparatus according to claim 1, wherein
the plurality of directions include rotational directions about horizontal and vertical axes orthogonal to each other;
the moving mechanism includes a rotary holder that holds the moving body such that the moving body is rotatable about the horizontal axis, and a grip supported by the rotary holder such that the grip rotates integrally with the moving body; and the force direction detection means detects a force in the rotational direction about the horizontal axis applied to the grip.

6. The holding mechanism for an X-ray imaging apparatus according to claim 5, wherein
the moving mechanism includes a support rod that supports the rotary holder such that the rotary holder is rotatable about the vertical axis; and
the force direction detection means detects forces in the rotational directions about the horizontal and vertical axes applied to the grip.

7. The holding mechanism for an X-ray imaging apparatus according to claim 6, wherein the force direction detection means includes a force detector disposed between the grip and the rotary holder and capable of detecting moments about a plurality of orthogonal axes.

8. The holding mechanism for an X-ray imaging apparatus according to claim 1, wherein
the plurality of directions include horizontal and vertical translational directions orthogonal to each other, and rotational directions about horizontal and vertical axes orthogonal to each other; and
the force direction detection means includes a force detector capable of detecting forces in the translational directions of three orthogonal axes and moments about the axes.

9. The holding mechanism for an X-ray imaging apparatus according to claim 1, further comprising an operator detection means that detects an operator; wherein
the permission direction determination means controls the switching means to prohibit the movement when the operator is not detected by the operator detection means, and determines the direction in which the movement is permitted by the switching means when the operator is detected.

10. The holding mechanism for an X-ray imaging apparatus according to claim 9, wherein
the moving mechanism includes a grip that moves integrally with the moving body; and
the operator detection means detects that the grip is gripped by the operator.

11. The holding mechanism for an X-ray imaging apparatus according to claim 10, wherein the operator detection means includes a communicator capable of wireless communication with a communication means held by the operator, and detects the operator via the communicator.

12. The holding mechanism for an X-ray imaging apparatus according to claim 1, further comprising:
a force strength detection means that detects a magnitude of the force applied to the moving mechanism; and
an assisting means that applies an assisting force in a movement direction of the moving body to the moving body based on a detected magnitude of the force.

13. The holding mechanism for an X-ray imaging apparatus according to claim 12, wherein
the plurality of directions include horizontal and vertical translational directions orthogonal to each other;
the moving mechanism includes a support rod that holds the moving body such that the moving body is translatable in a vertical direction, and a grip supported by the support rod such that the grip moves integrally with the moving body; and
the force strength detection means detects a force in the vertical direction applied to the grip.

14. The holding mechanism for an X-ray imaging apparatus according to claim 13, wherein
the moving mechanism includes a traveling mechanism that supports the support rod such that the support rod is translatable in a horizontal direction; and
the force strength detection means detects forces in the horizontal and vertical translational directions applied to the grip.

15. The holding mechanism for an X-ray imaging apparatus according to claim 12, wherein
the plurality of directions include rotational directions about horizontal and vertical axes orthogonal to each other;
the moving mechanism includes a rotary holder that holds the moving body such that the moving body is rotatable about the horizontal axis, and a grip supported by the rotary holder such that the grip moves integrally with the moving body; and
the force strength detection means detects a force in the rotational direction about the horizontal axis applied to the grip.

16. The holding mechanism for an X-ray imaging apparatus according to claim 15, wherein
the moving mechanism includes a support rod that supports the rotary holder such that the rotary holder is rotatable about the vertical axis; and
the force strength detection means detects forces in the rotational directions about the horizontal and vertical axes applied to the grip.

17. The holding mechanism for an X-ray imaging apparatus according to claim 12, further comprising a force detector that detects the direction of the force and the magnitude of the force; wherein
the force detector includes the force direction detection means and the force strength detection means that are integral and unitary with each other.

18. The holding mechanism for an X-ray imaging apparatus according to claim 12, wherein the assisting means applies, to the moving body, the assisting force having a magnitude corresponding to the detected magnitude of the force.

19. The holding mechanism for an X-ray imaging apparatus according to claim 1, wherein
the moving mechanism includes an engagement means that releasably engages with the moving mechanism to stop the moving body at a predetermined position;
the switching means switches to a state of prohibiting the movement of the moving body when the moving mechanism engages with the engagement means; and
the permission direction determination means determines the direction in which the movement is permitted by the switching means, and disengages the moving mechanism from the engagement means.

20. The holding mechanism for an X-ray imaging apparatus according to claim 19, further comprising:
a force strength detection means that detects a magnitude of the force applied to the moving mechanism; and
an assisting means that applies an assisting force in a movement direction of the moving body to the moving body based on a detected magnitude of the force; wherein
the assisting means decreases the assisting force to be applied to the moving body as the moving body is closer to the predetermined position when the moving body moves toward the predetermined position.

21. The holding mechanism for an X-ray imaging apparatus according to claim 1, further comprising a free mode setting means that controls the switching means to permit the movement of the moving body in all of the plurality of directions based on a setting operation of an operator.

22. The holding mechanism for an X-ray imaging apparatus according to claim 21, wherein the free mode setting means switches the switching means to a state of prohibiting the movement in all of the plurality of directions based on a setting cancellation operation of the operator or a passage of time after permission of the movement in all of the plurality of directions.

23. The holding mechanism for an X-ray imaging apparatus according to claim 1, wherein
the permission direction determination means:
acquires a reference position of the moving body based on the imaging method information; and
in the automatic determination control, permits the movement of the moving body in a movement direction in which a current position of the moving body is different from the reference position among the plurality of directions, based on the detected direction of the force, and prohibits the movement of the moving body in the movement direction in which the current position of the moving body coincides with the reference position.

24. The holding mechanism for an X-ray imaging apparatus according to claim 1, wherein
the permission direction determination means:
acquires imaging site information indicating a site to be imaged in X-ray imaging; and
switches, according to the imaging site information, between automatic determination control of determining the direction in which the movement is permitted based on the detected direction of the force and manual determination control of determining the direction in which the movement is permitted based on an operation input by an operator.

25. The holding mechanism for an X-ray imaging apparatus according to claim 24, wherein
the permission direction determination means:
acquires a reference position of the moving body based on the imaging site information; and
in the automatic determination control, permits the movement of the moving body in a movement direction in which a current position of the moving body is different from the reference position among the plurality of directions, based on the detected direction of the force, and prohibits the movement of the moving body in the movement direction in which the current position of the moving body coincides with the reference position.

26. The holding mechanism for an X-ray imaging apparatus according to claim 1, wherein the switching means is constantly maintained in the state of prohibiting the movement of the moving body in each of the plurality of directions, and is switched to a state of individually permitting the movement of the moving body in the direction determined by the permission direction determination means.

27. The holding mechanism for an X-ray imaging apparatus according to claim 26, wherein the switching means includes a plurality of locking mechanisms respectively corresponding to the plurality of directions and that lock the movement of the moving body, and unlocks one of the locking mechanisms corresponding to the direction determined by the permission direction determination means.

28. An X-ray imaging apparatus comprising:
a moving body including an X-ray tube;
an X-ray detector;
a moving mechanism that holds the moving body such that the moving body is movable in a plurality of directions;
a locking mechanism that switches between a state of permitting movement of the moving body and a state of prohibiting the movement in each of the plurality of directions;
a force detector that detects a direction of a force applied to the moving mechanism; and
a controller configured to
determine a direction in which the movement is permitting by the locking mechanism among the plurality of directions based on the force detected by the force detector,
acquire imaging method information selected from two or three options among imaging in an upright position, imaging in a recumbent position, and general imaging, and
switch, according to the imaging method information, between automatic determination control of determining the direction in which the movement is permitted based on the detected direction of the force and manual determination control of determining the direction in which the movement is permitted based on an operation input by an operator.

* * * * *